United States Patent [19]
Peterson

[11] Patent Number: 5,939,330
[45] Date of Patent: Aug. 17, 1999

[54] METHOD AND APPARATUS FOR GATHERING AND PREPARING LIQUID SAMPLES FOR ANALYSIS

[76] Inventor: Roger Peterson, County Rd. 375, Old Ocean, Tex. 79463

[21] Appl. No.: 08/828,655

[22] Filed: Mar. 31, 1997

Related U.S. Application Data

[63] Continuation-in-part of application No. 08/692,018, Aug. 2, 1996, Pat. No. 5,794,695, and application No. 08/795,147, Feb. 7, 1997, Pat. No. 5,839,509.

[51] Int. Cl.$^6$ .............................. G01N 35/10; G01N 1/10
[52] U.S. Cl. .......................... 436/180; 436/43; 436/52; 436/174; 436/179; 422/62; 422/63; 422/68.1; 422/81
[58] Field of Search .................... 436/180, 174, 436/179, 43, 52; 422/62, 63, 68.1, 81

[56] References Cited

U.S. PATENT DOCUMENTS

| | | |
|---|---|---|
| 3,690,833 | 9/1972 | Ferrari ...................................... 422/81 |
| 3,733,177 | 5/1973 | Klein ....................................... 436/180 |
| 3,846,075 | 11/1974 | Cioffi ........................................ 422/81 |
| 4,108,602 | 8/1978 | Hanson et al. ............................ 422/81 |
| 4,472,354 | 9/1984 | Passell et al. ............................. 422/62 |
| 4,705,669 | 11/1987 | Tsuji et al. ................................ 422/93 |
| 5,108,928 | 4/1992 | Menard et al. ........................... 436/43 |
| 5,192,509 | 3/1993 | Surjaatmadja et al. ................... 422/75 |
| 5,230,863 | 7/1993 | Salpeter .................................... 422/67 |
| 5,695,720 | 12/1997 | Wade et al. ............................... 422/82 |
| 5,773,297 | 6/1998 | Benson et al. ............................ 436/52 |

*Primary Examiner*—Long V. Le
*Attorney, Agent, or Firm*—Gunn & Associates, P.C.

[57] ABSTRACT

The apparatus gathers and prepares liquid samples for analysis for elements or compounds within the liquid samples such as water samples for tritium analysis. This disclosure is further directed toward apparatus and methods for the gathering or collecting of water samples from underground formations penetrated by a borehole, or collecting water samples at varying depths in surface canals, ponds, and the like. The invention is particularly suited for monitoring water in the vicinity of nuclear manufacturing, fabrication and disposal facilities for tritium contamination of ground waters.

19 Claims, 25 Drawing Sheets

METHOD AND APPARATUS FOR GATHERING AND PREPARING LIQUID SAMPLES FOR ANALYSIS

This is a continuation in part of patent application Ser. No. 692,018 filed Aug. 2, 1996, now U.S. Pat. No. 5,794,695 and also Ser. No. 795,147 filed Feb. 7, 1997 now U.S. Pat. No. 5,839,509.

BACKGROUND OF THE INVENTION

This invention is directed toward apparatus and methods for gathering and preparing liquid samples for analysis, and more specifically directed toward the gathering and preparing of water samples for analysis for tritium content, where the samples are collected from underground formations penetrated by a borehole or collected at varying depths in surface canals and the like. The monitoring of liquid samples for contaminants is quite common in today's industrialized society. Such monitoring is carried out to track the efficiency of various manufacturing processes. In addition, such monitoring is employed to monitor potential hazards to humans and to the environment resulting from various manufacturing and processing operations.

Many types of nuclear manufacturing and processing facilities were built in significant numbers starting in the late 1940's and early 1950's. In the following decades, even more such facilities were built world wide as a result of the proliferation of nuclear power, nuclear weaponry, and nuclear medicine. As with most manufacturing and processing operations, nuclear facilities generate wastes which can be hazardous to the environment and to the human and animal population, and such wastes must be monitored and disposed using methods which minimize health and environmental risks.

Attention is now directed toward nuclear facilities designed for the manufacture of nuclear weapons. More particularly, attention is directed toward "fission" weapon facilities used to produce weapons based upon induced neutron "chain" reactions in certain isotopes of uranium and plutonium. Great quantities of energy are released as a result of the induced chain reaction which is often referred to as an "atomic explosion". It is well known that one precursor for such an energy release or explosion is a "critical mass" of the fission material in order to sustain the chain reaction. Weapons designers also found in the 1940's that more efficient energy releases or explosions could be obtained if the chain reaction were initiated with a burst of neutrons from a device known in the art as a "trigger".

Several techniques have been used in nuclear weapons to construct triggers which produce large neutron fluxes for relatively short periods of time. The most common trigger is based upon the reaction $$H^2+H^3=He^4+n$$

where $H^2$ = deuterium which is a hydrogen atom with a nucleus containing a neutron as well as a proton;

$H^3$ = tritium which is a hydrogen atom with a nucleus containing two neutrons as well as a proton;

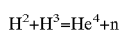

-continued $He^4$ = helium; and n = a neutron

That is, when tritium is bombarded with deuterium at a sufficient energy, a nuclear reaction occurs which yields helium, plus a neutron with approximately 14 million electron volts (MeV) of energy. Triggers based upon this "deuterium-tritium" reaction therefore produce the neutron flux desired as a trigger for fission type weapons.

Tritium is used at fission type weapons manufacturing facilities and, as might be expected, most of these manufacturing facilities produce significant amounts of tritium. Tritium is radioactive with a half life of approximately 12.33 years, and decays to ground state $He^3$ by the emission of a beta particle. Tritium reacts chemically as "normal" hydrogen ($H^1$). It is well known that hydrogen is easily ingested by plant life and animal life including humans. Tritium is likewise easily ingested, but tritium ingestion results in the possible chemical binding of radioactive tritium within the plant or animal organism. As an example, tritium ingested by a human would result in radioactive tritium atoms being chemically bound or "lodged" within the human. Subsequently, as the tritium decays with a half life of 12.33 years, beta particles are emitted at the sites of the bound tritium causing significant biological and cellular damage in the area of emission. It is apparent, therefore, that waste liquid, such as water which is contaminated with tritium, can be a significant health threat to humans and to the environment. Such tritium contaminated water can be found in cooling ponds and drainage canals in the vicinity of nuclear facilities such as nuclear weapons plants. Furthermore, run-off water, which migrates and percolates into the earth around nuclear facilities, can also be contaminated with tritium. This becomes an especially critical problem if these contaminated waters migrate into drinking water aquifers. The result is a potable aquifer contaminated with a beta emitting tritium with a half life of 12.33 years.

Nuclear sites are currently monitored for tritium wastes. Liquid samples such as water are collected at varying depths from cooling ponds or canals. To monitor the migration of tritium contaminated water toward the water tables, test wells are often drilled about the site, ground water is allowed to flow into each of these wells, and water samples are taken at varying depths within the well. As an example, the detection of tritium contamination in a water sample gathered near the surface usually indicates that contaminated water has not migrated to deeper aquifers. Furthermore, the combination of tritium concentration measurements made at multiple depths in multiple wells can be used to generate a three dimensional map of any tritium contamination in the ground beneath the nuclear facility. Since nuclear facilities can be quite large and cover hundreds if not thousands of acres, it should be understood that tens or even hundreds of monitor wells are required to properly monitor water movement and possible ground water contamination.

Again, examining current tritium monitoring techniques, liquid samples gathered from monitor wells, or at different depths within surface ponds or canals, must be pretreated prior to analysis for tritium. In one such pretreatment, the water is passed through a column containing a plurality of resin materials in order to remove certain cations and other materials which prohibit accurate tritium concentration measurements. This pretreatment can be performed at the sample site, but, using current technology, is preferably performed at a remote, analytical laboratory under controlled conditions. Tritium analysis is currently being performed at the remote, analytical laboratory. The time required to perform this type of analysis often takes one to two months from the time samples are received. The analysis cost per sample is also quite high. Considering that multiple sample sites such as monitor wells are needed, and that samples should be taken at varying depths at each sample site, the total cost of a monitor survey can be quite high. Furthermore, it is highly desirable to sample at a given site, such as a monitor well, as many as three to four times per day, in order to detect early, any tritium contamination so that remedial actions can be taken immediately. Although sampling at this time frequency can be done today, the current sample analysis turnaround of one to two months negated the usefulness of this method.

SUMMARY OF THE INVENTION

The invention is directed toward apparatus and methods for gathering and preparing liquid samples for analysis for elements or compounds within the liquid samples. Although applicable to a variety of liquids and to a variety of elements or compounds, the preferred embodiment of the invention is directed toward the gathering and pretreating of water samples for tritium analysis. This disclosure is further directed toward apparatus and methods for the gathering or collecting of water samples from underground formations penetrated by a borehole, or collecting water samples at varying depths in surface canals, ponds, and the like. The invention is particularly suited for monitoring water in the vicinity of nuclear manufacturing, fabrication and disposal facilities for tritium contamination of ground waters.

The sampling system includes submersible pumps and a vacuum/compressor system and valving system for operating these pumps in order to gather liquid samples at varying depths below the surface of the earth, and transporting these samples to the surface of the earth for pretreatment prior to analysis for contaminants. For purposes of discussion, it will be assumed that the liquid is water and that the contaminant is tritium.

Although the system can be used to sample only one location, one of its main advantages is that multiple locations can be sequentially sampled or "monitored" for tritium contamination. As mentioned previously, the system can be used to obtain samples from below the surface, such as water samples from subterranean wells, from cooling ponds, canals and the like. Again, for purposes of discussion, it will be assumed that the water samples are being obtained at varying depths in a plurality of well boreholes. Each well is preferably lined or "cased" with a steel, plastic or composite liner to prevent the respective boreholes from caving in. A submersible pump is positioned within each well, and water samples from each well are taken by the submersible pumps sequentially and automatically under the control of a microprocessor and timer. The valving system of each submersible pump includes a spring loaded check valve which can be set to operate at above a certain hydraulic pressure. This, in turn, allows a given pump to obtain a water sample only below a given depth corresponding to the selected hydrostatic pressure. This feature allows sampling at varying, preselected depths as will be discussed in detail is a subsequent section of this disclosure.

Samples from each pump, therefore each well, are transferred or "evacuated" to the surface for pretreating and analysis. The compressor/vacuum pump system cooperating with a valving system, which also includes flow lines, is used to transfer the samples to the surface. Specifics of the operation of the valving system will subsequently be presented in detail. At this point, it suffices to say that the vacuum/compressor system and the valving system, under the control of the microprocessor and timer, are used to control the flow of the sample water. Furthermore, these systems are also used to flow purge air and wash water within the sample in order to clean the system between sampling sequences so that the next sample will not be contaminated by the previous sample.

While the earlier disclosures include a carousel mechanism selecting one of a plurality of columns sample water is pretreated for testing for tritium. The term "pretreated" is used to delineate this step of the analysis from any "treatment" of the sample that might be required in the analysis of the sample within a tritium analyzer. This improved mechanism includes a set of similar valves cooperating with cylinder and piston devices powered by the compressor/vacuum pump system under a controller which, in turn, is under control of the system microprocessor and timer. This feature of the invention greatly increases the speed and automation of the pretreatment phase of the sampling and analysis process.

Once each collected water sample has been treated in a specific sample pretreatment column in the carousel, the sample is then passed to an analyzer for analysis by means of the valving system and its accompanying flow lines. This transfer is also under control of the system microprocessor and timer, which cooperates with the analyzer by means of communication signals. Tritium concentration is preferably measured with a chromatographic analyzer such as a Radiomatic HPLC high precision liquid chromatographic unit. Results of each sample analysis are displayed with an appropriate analog or digital meter, printed by means of a printer, or recorded on a magnetic disk or other digital recording device.

All of the previously discussed elements of the system, with the exception of the submersible pumps and some elements of the valving system and flow lines, are preferably located at the surface of the earth. The plurality of submersible pumps of the invention rapidly and automatically obtain samples and transfer these samples to the surface for pretreatment and analysis. The pumps are also automatically purged after sample transfer such that the next sample will not be contaminated by the previous sample.

The invention also provides rapid and automatic means for pretreating each sample prior to analysis by using the carousel mechanism in cooperation with the valving system and the system microprocessor and timer. This means increases the accuracy and precision of the overall analysis method, while reducing cost by eliminating the need for manual sample pretreatment. Furthermore, the samples can be pretreated on site thereby reducing the overall sampling and analysis time when compared with current methods.

The valving system (at the surface) for the submersible pumps collects the sample from any selected sample site. Furthermore, the system microprocessor and timer gets multiple samples sequentially in time. Since the entire sampling and pretreatment system is fast, efficient and automatic, each sample site can be sampled and analyzed as often as needed, even three to four times per day. This makes the system ideally suited for monitoring tritium at facilities where contamination can be sudden. As an example, using a four times per day sampling, the maximum time interval between samples is six hours. Since sample pretreating and analysis typically takes approximately thirty minutes, the maximum time that can elapse after contamination, such as a spill, is slightly more than six hours. This rapid detection capability of the invention permits rapid remedial action to be taken, especially when compared with typical one to two month sample analysis turnaround times of present, off site, commercial tritium analysis services.

In summary, the sequence of sample acquisition and sample pretreatment events, described briefly above, are controlled by the system microprocessor and timer thereby eliminating need for direct human operation. This substantially reduces the cost and increases the accuracy of sampling and pretreating compared to present human operated systems. The entire sampling, pretreatment and analysis sequence requires less than thirty minutes thereby analysis results can be obtained very rapidly when compared with present, commercial, off site tritium analysis services. The entire sampling and pretreatment system is relatively small and portable, as is the preferred analyzer. Sample analysis can therefore be obtained on site within thirty minutes compared with the typical one to two month turn-around of present, commercial, off site analysis services.

BRIEF DESCRIPTION OF THE DRAWINGS

So that the manner in which the above recited features, advantages and objects of the present invention are attained and can be understood in detail, more particular description of the invention, briefly summarized above, may be had by reference to embodiments thereof which are illustrated in the appended drawings.

DETAILED DESCRIPTION OF THE PREFERRED EMBODIMENT

The two parent applications set forth a system in general terms while the 25 similar views diagram the sampling and pretreating system which cooperates with a tritium analyzer. Building on the prior disclosures, specific structural aspects are first noted in FIG. 1 and then the 25 steps in detail will be reviewed.

Figure 1:
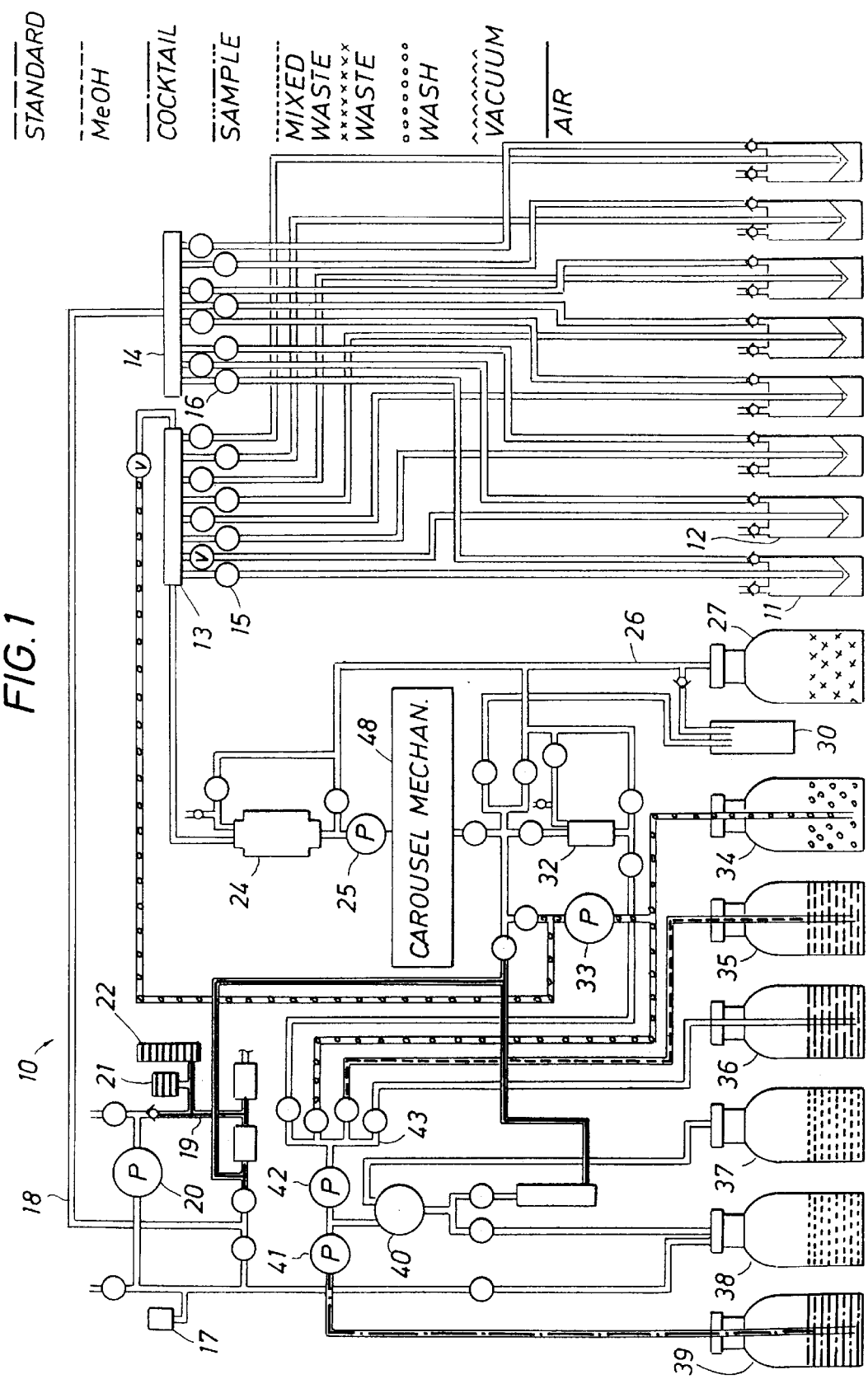
FIGS. 1 to 25 show the same schematic connections for a sampling, pretreatment and analyzer and shows a progression of operative steps in the system.

Going first to FIG. 1 of the drawings, it will be noted that this description of the apparatus can be extended to all the other views.

The 25 views are incorporated to make the explanation of operation easier. They show a suggested sequence of operations. More will be noted regarding operations and alternative sequences of operation in substantial detail later.

The system shown in FIG. 1 accomplishes testing as set forth in the earlier disclosures. It collects a set of samples, provides pretreatment and then tests for radiation. This is especially useful in testing ground water and other sources of water for the radioactive hydrogent, namely, tritium. The numeral 10 in FIG. 1 refers generally to the entire system. It cooperates with a first pump 11 and a second pump 12. Others are shown, and the number can be increased indefinitely. Typically, the pumps 11 and 12 are located underground in wells having a depth which is determined by the sampling requirements for the region. The pumps 11 and 12 operation in the fashion set forth in the foregoing disclosures. Those disclosures are incorporated by reference.

The pumps 11 and 12 are installed to selectively deliver a measured quantity of sample. The pumps 11 and 12 are configured and scaled so that the requisite quantity is obtained. A typical operational mode recovers about 50 cc of the water sample. For test purposes, typically only about 10 cc is required for the specific test. Again, this is a scale factor and relates to the size of the test instrument and other aspects.

Each of the pumps 11, 12 and the others which are unnumbered, is connected with two lines. The lines extend collectively to first and second manifolds 13 and 14. These manifolds, similar in construction, connect with a number of valves 15 and 16 which are replicated. FIG. 1 shows the system installed with N wells where N is a whole number integer, and the manifolds 13 and 14 include N valves on each manifold. This enables control of the system through the valves 15 and 16 on the manifolds. These valves are preferably provided with valve operators (omitted for sake of clarity) and they are opened and closed in response to a controller to be described. Indeed, FIG. 1 shows many valves in the system and each valve is provided with an operator. All the operators have been omitted for sake of clarity. The specific operation of the many valves included in FIG. 1 is timed by virtue of the control signals applied to the operators. Rather than show valve operation in a timing chart or other logic table, it is perhaps more helpful in operation by presenting this format, namely, the 25 sequential steps shown in operation. As will be understood, this is one way in which the system 10 can be operated. Equally so, it is not the only way in which the system 10 can be operated.

As will be further understood, the manifold 14 operates as a vacuum source. The manifold 14 is provided with vacuum controlled by a vacuum switch 17 which is communicated through a vacuum line 18 to the manifold 14. By the appropriate provision of vacuum through the manifold 14, a particular pump chamber 11, 12 or any of the N pumps are then filled.

The vacuum switch 17 prompts operation of the pump 20. On one side, the pump 20 provides vacuum, and the opposite side of the pump delivers air at pressure in the line 19. Just as the switch 17 triggers operation to provide vacuum, the switch 21 operates to assure delivery of air under pressure. Conveniently, a tank 22 is incorporated to accumulate air at an elevated pressure. This can speed up operation and reduce waiting time while the pump 20 builds up pressure.

The manifold 13 is the sample manifold. It is connected with a reservoir 24 which holds a measured quantity, typically 50 cc. While it can be scaled to a different size, it is provided with a control switch which measures filling to a specified level such as the suggested amount of 50 cc. In addition to that, it is connected with a pump 25. Surplus from the container 24 is delivered through a waste line 26 to a waste outlet 27.

For convenience at a different testing lab, the waste line 26 serves a dual purpose in that it connects through a branch to fill a sample container 30. The container 30 can be demounted and removed to another lab for testing for any purpose. Alternatively, the sample container 30 can be tagged with time and date of the sample and can be stored for archive purposes. In view of the fact that the tritium does decay, it is not easy to store for a long time radioactive samples if the half life of the radioactive elements in the container is relatively short. Storage in the container 30 is therefore subject to decay depending on the half life.

The sample container 32 is similar to the container 24 but smaller. It holds a requisite volume such as 10 cc. A pump 33 delivers a wash liquid from a wash liquid source 34. In addition to the container 34, there are other containers requiring mention. Briefly, the containers 35, 36 and 39 contain identified liquids. The containers 37 and 38 receive waste. The system further incorporates the counting cell 40 which will be described in greater detail. Pumps 41 and 42 are illustrated with pump 42 connected to a manifold 43. A carousel mechanism 48 better described in the disclosures incorporated by reference is also included for pretreatment.

Figure 2:
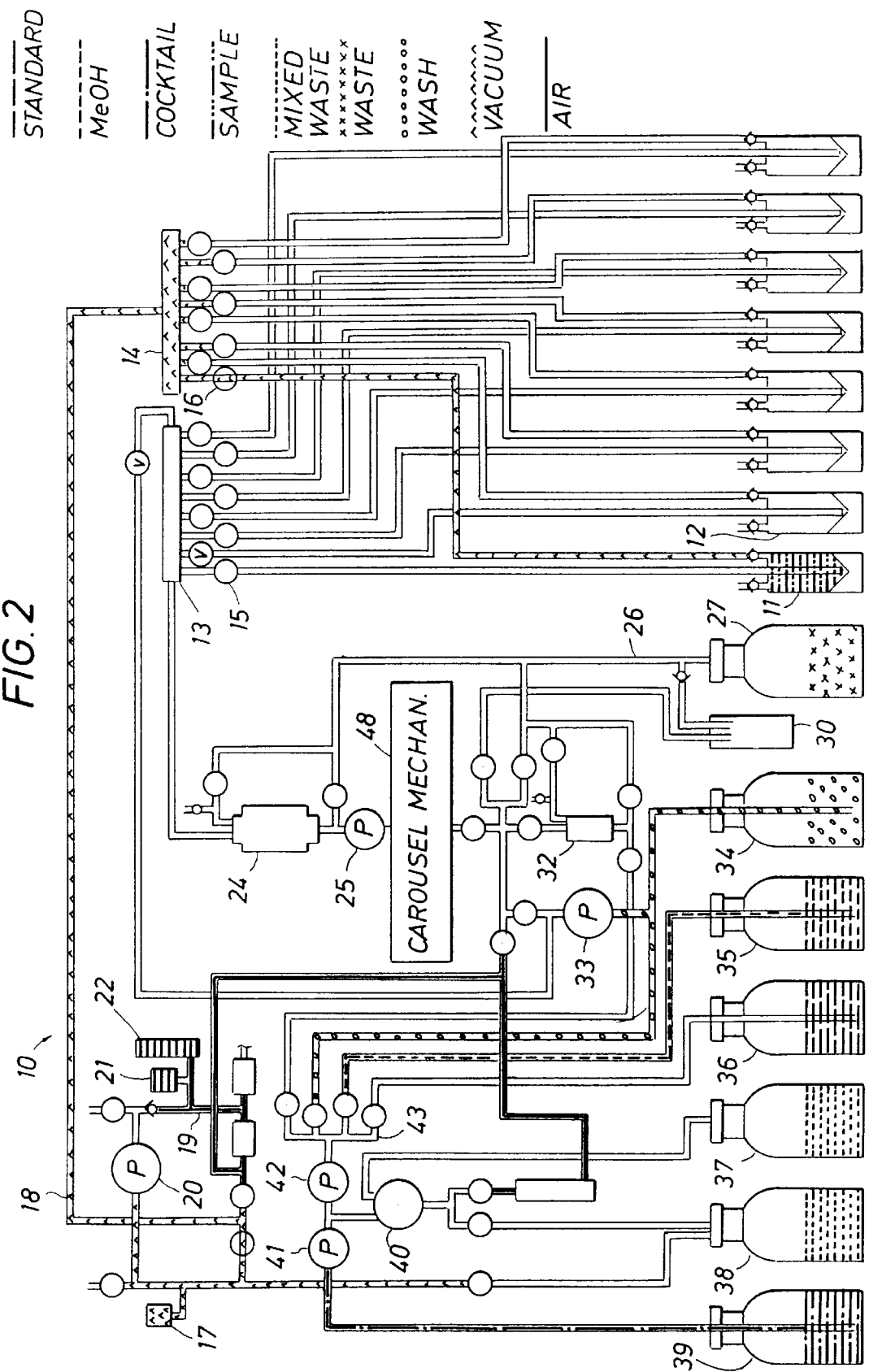

While the foregoing describes certain of the components the operation of the many valves shown in FIG. 1 is keyed to the sequence of flow patterns deployed in the 25 views. Proceeding therefore from FIG. 1, this shows the system in a state of readiness but prior to operation. This occurs when the equipment is on and operative but has not yet been switched for starting an operational sequence. Proceeding from FIG. 1 to FIG. 2, vacuum is applied through the line 18 and triggers filling of the pump 11. Wash is delivered from the container 34 through the pump 33 to be available for a later step.

Figure 3:
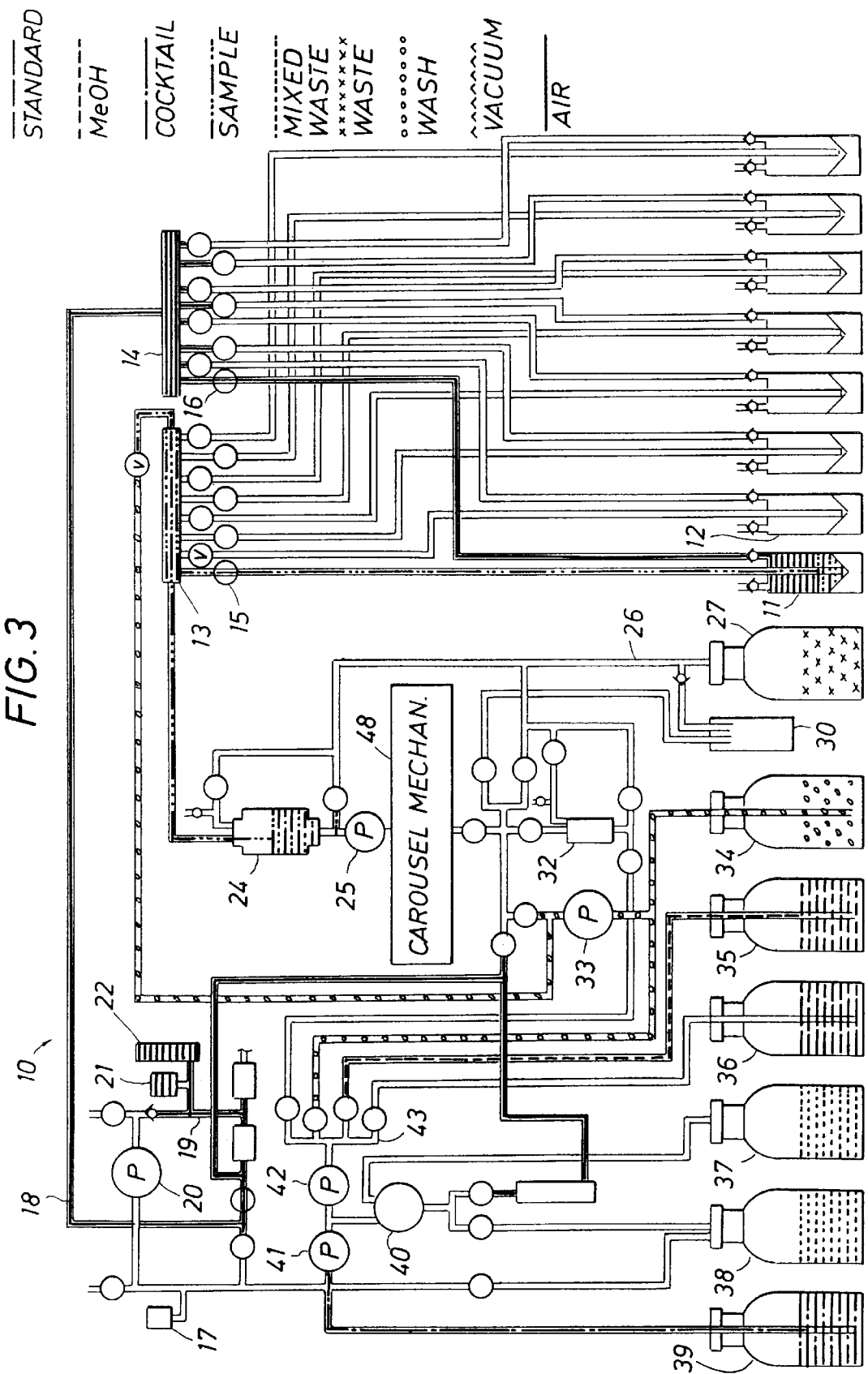
Figure 4:
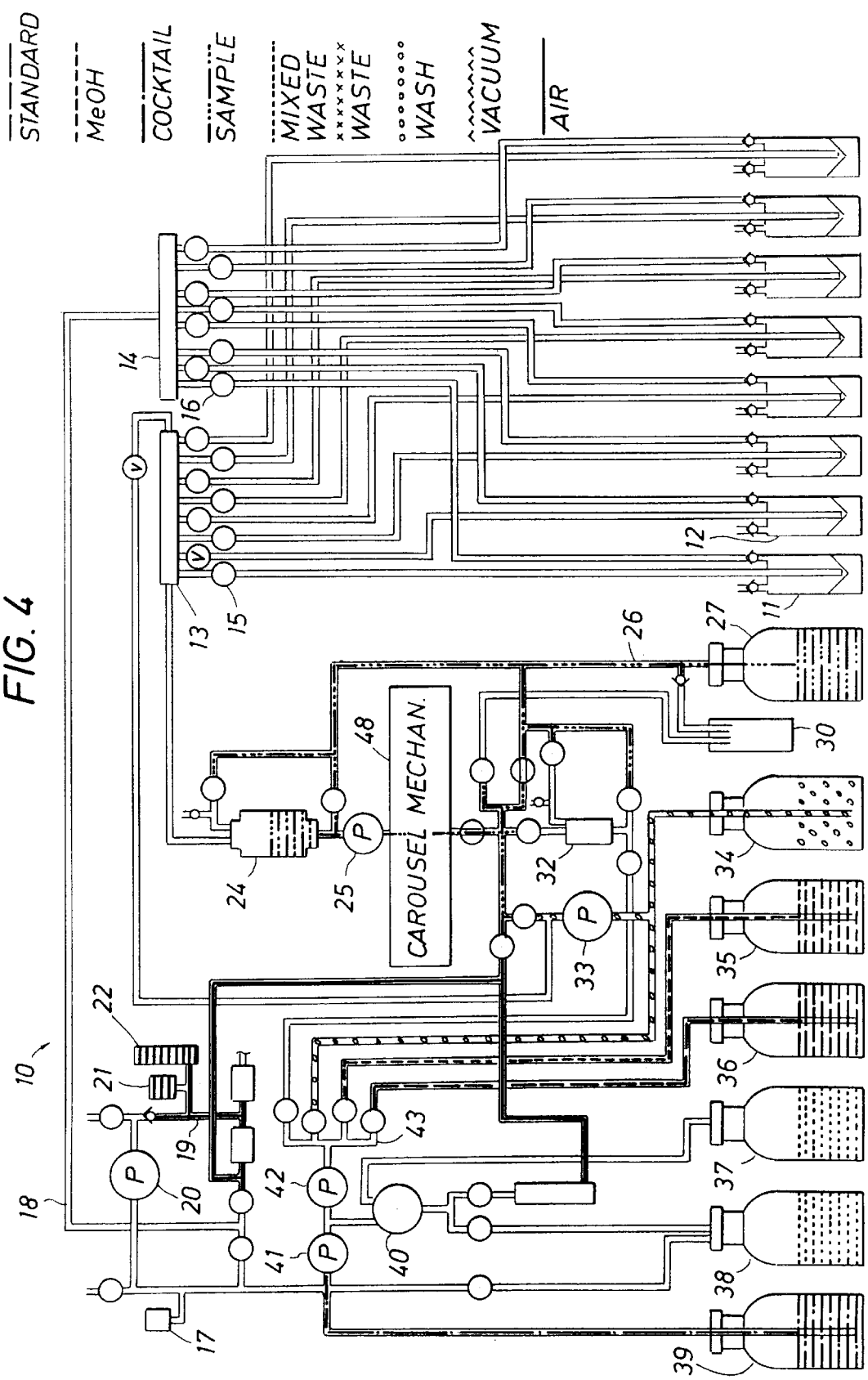
Figure 5:
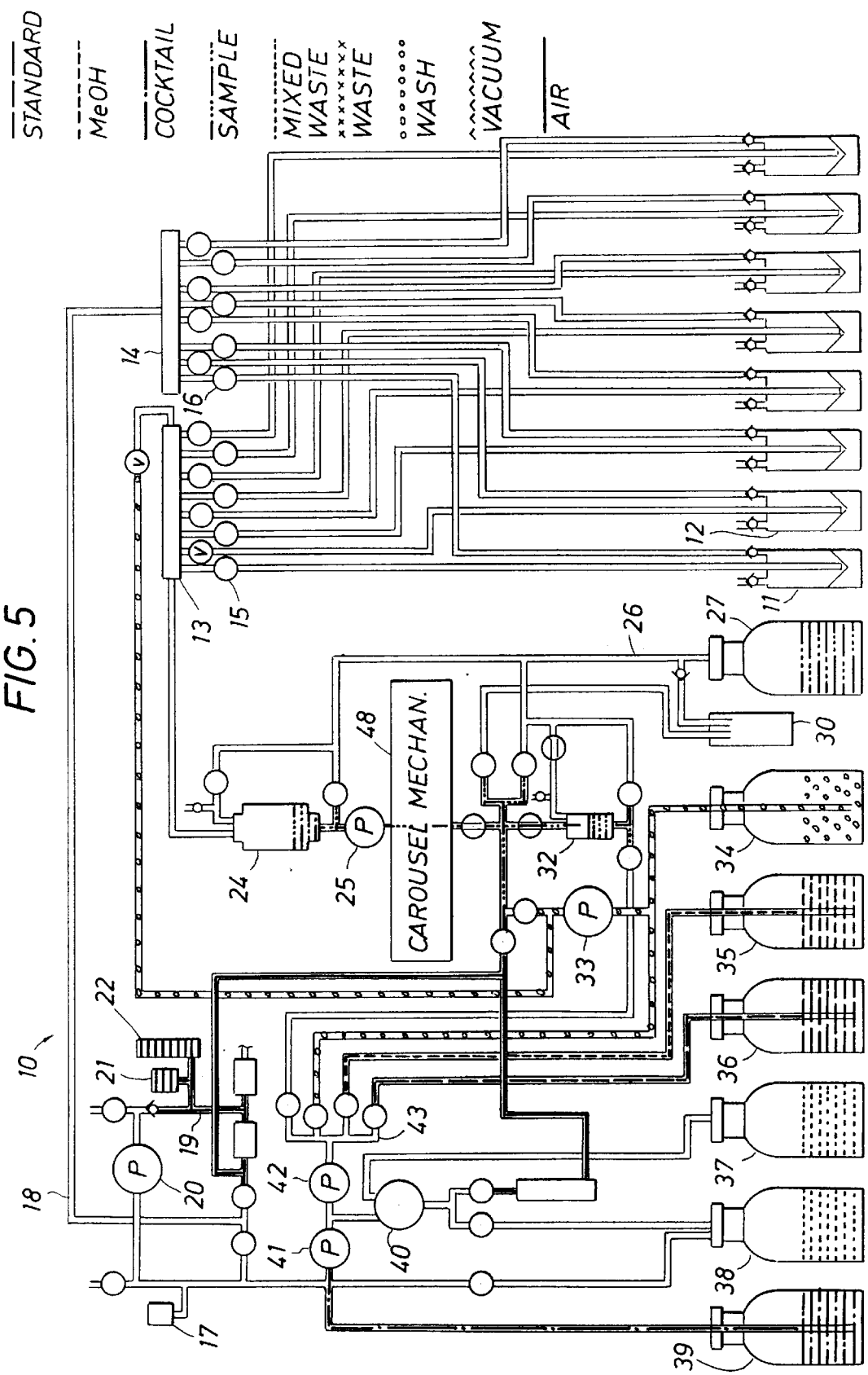
Figure 6:
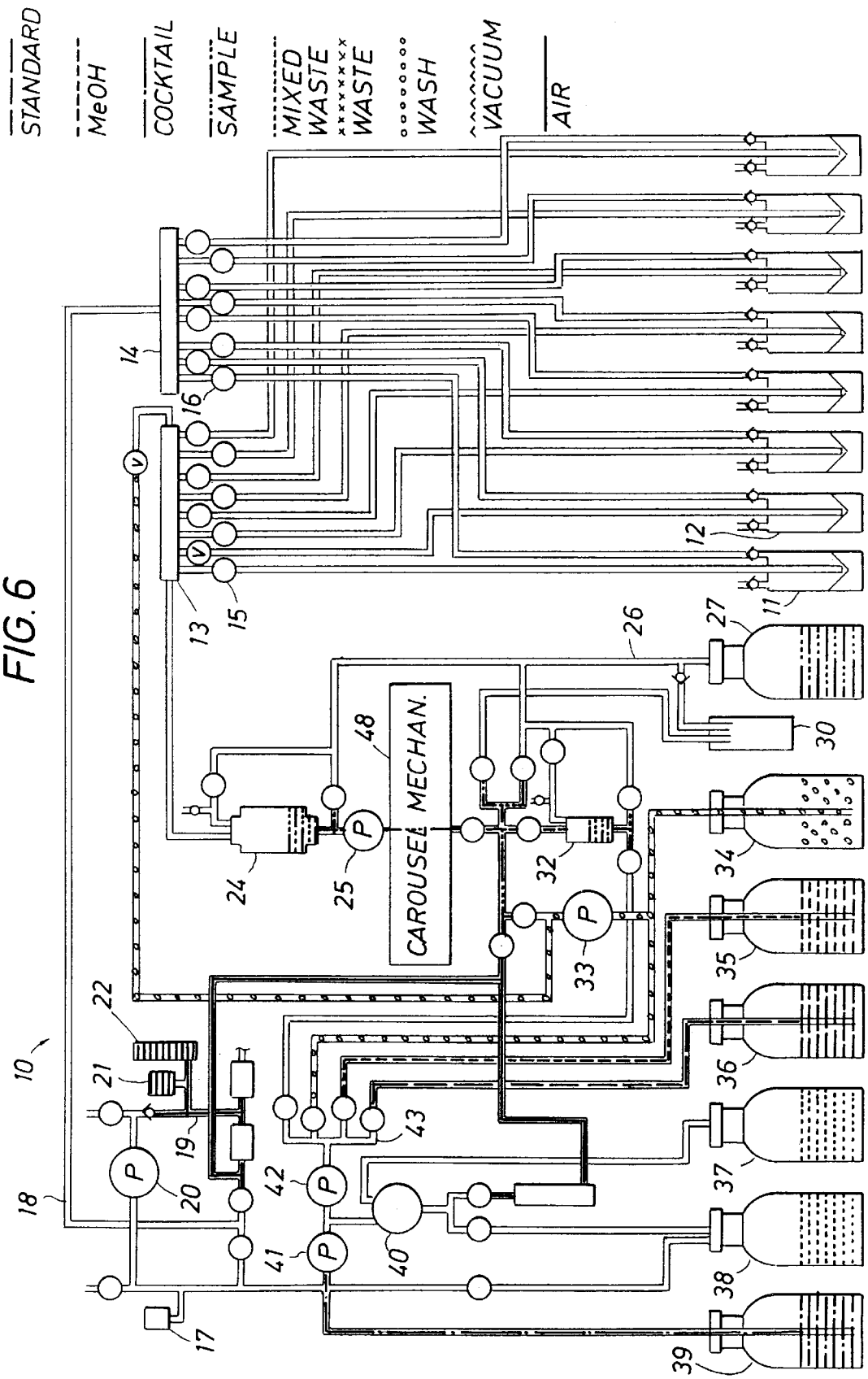
Figure 7:
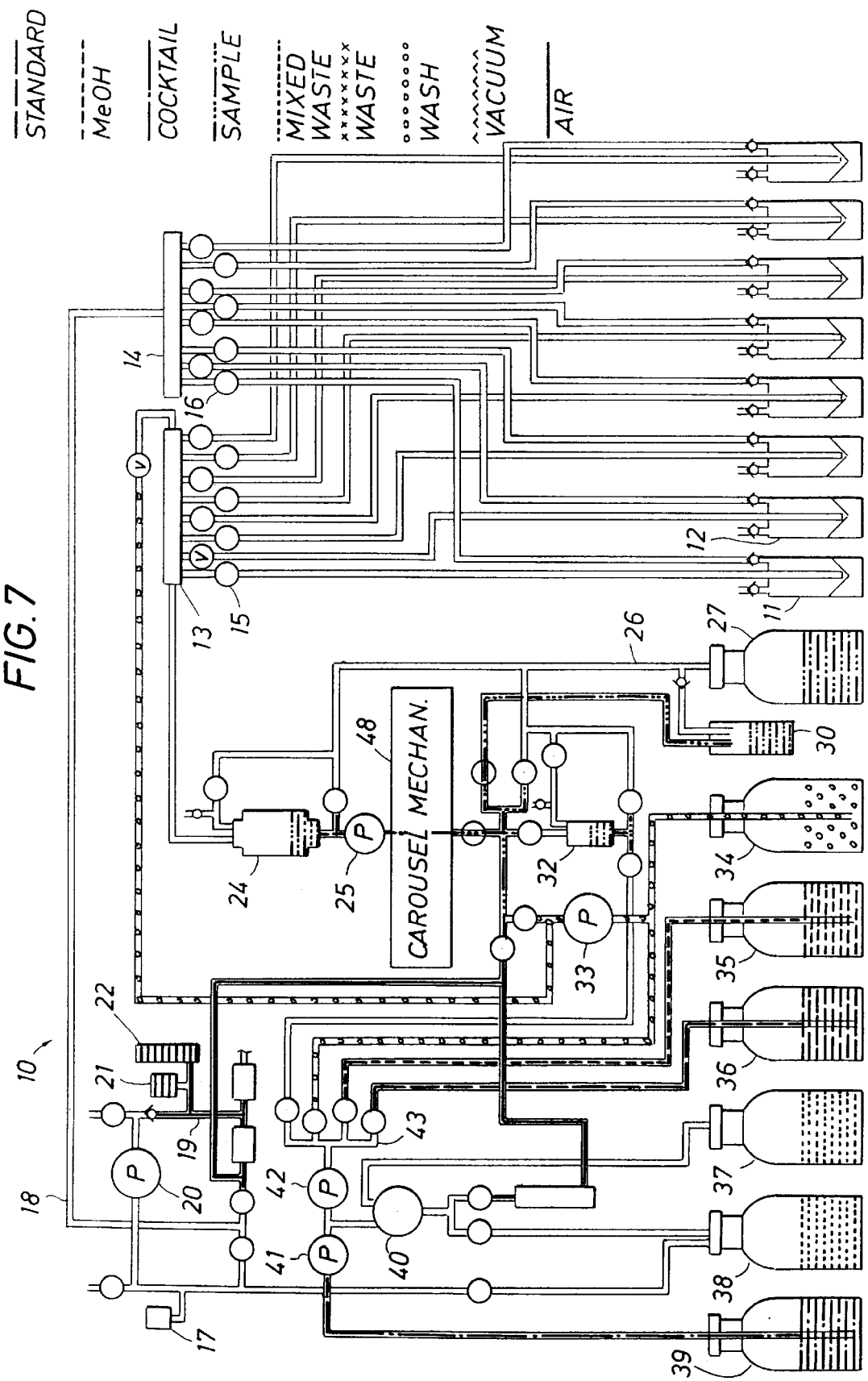
Figure 8:
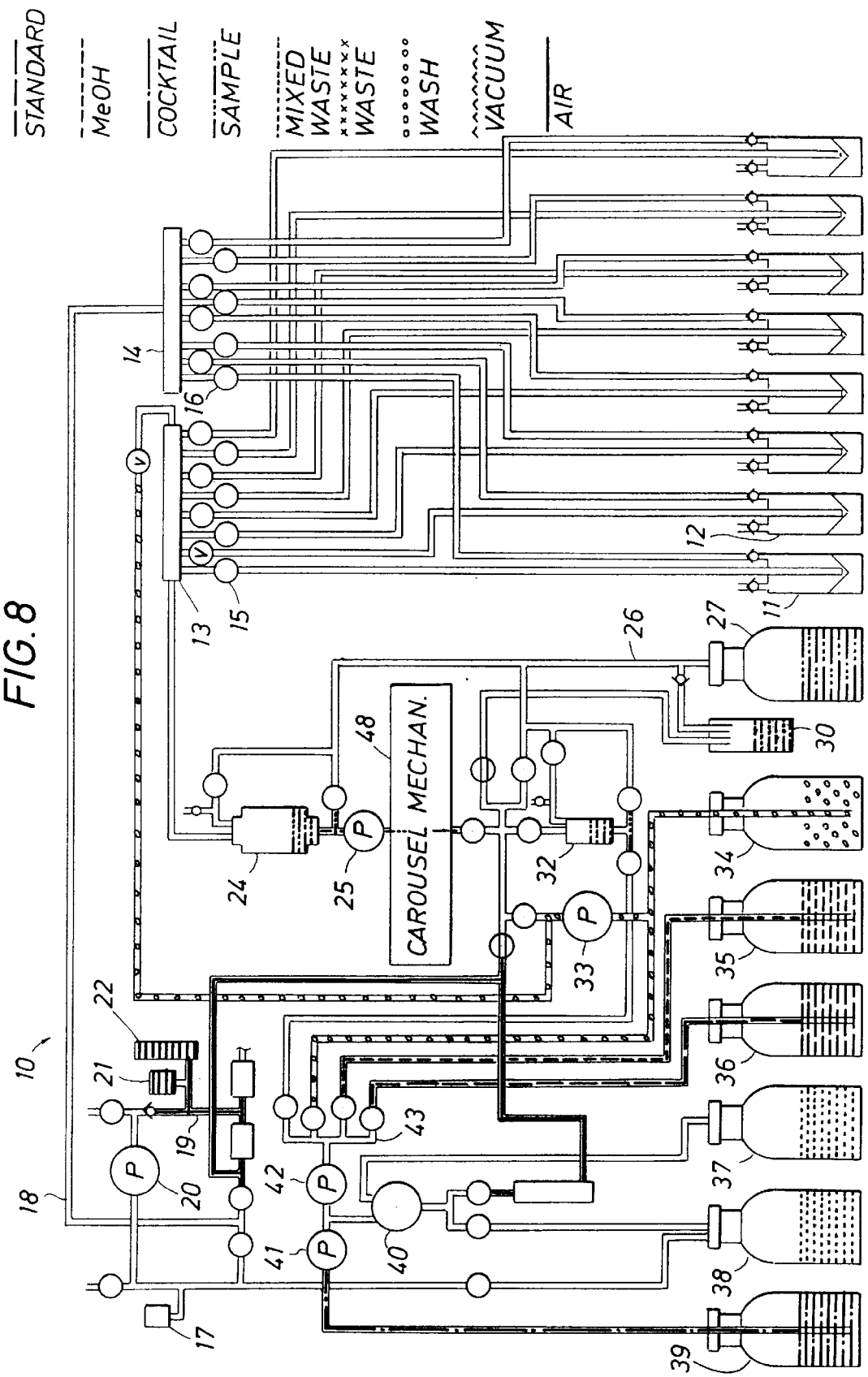
Figure 9:
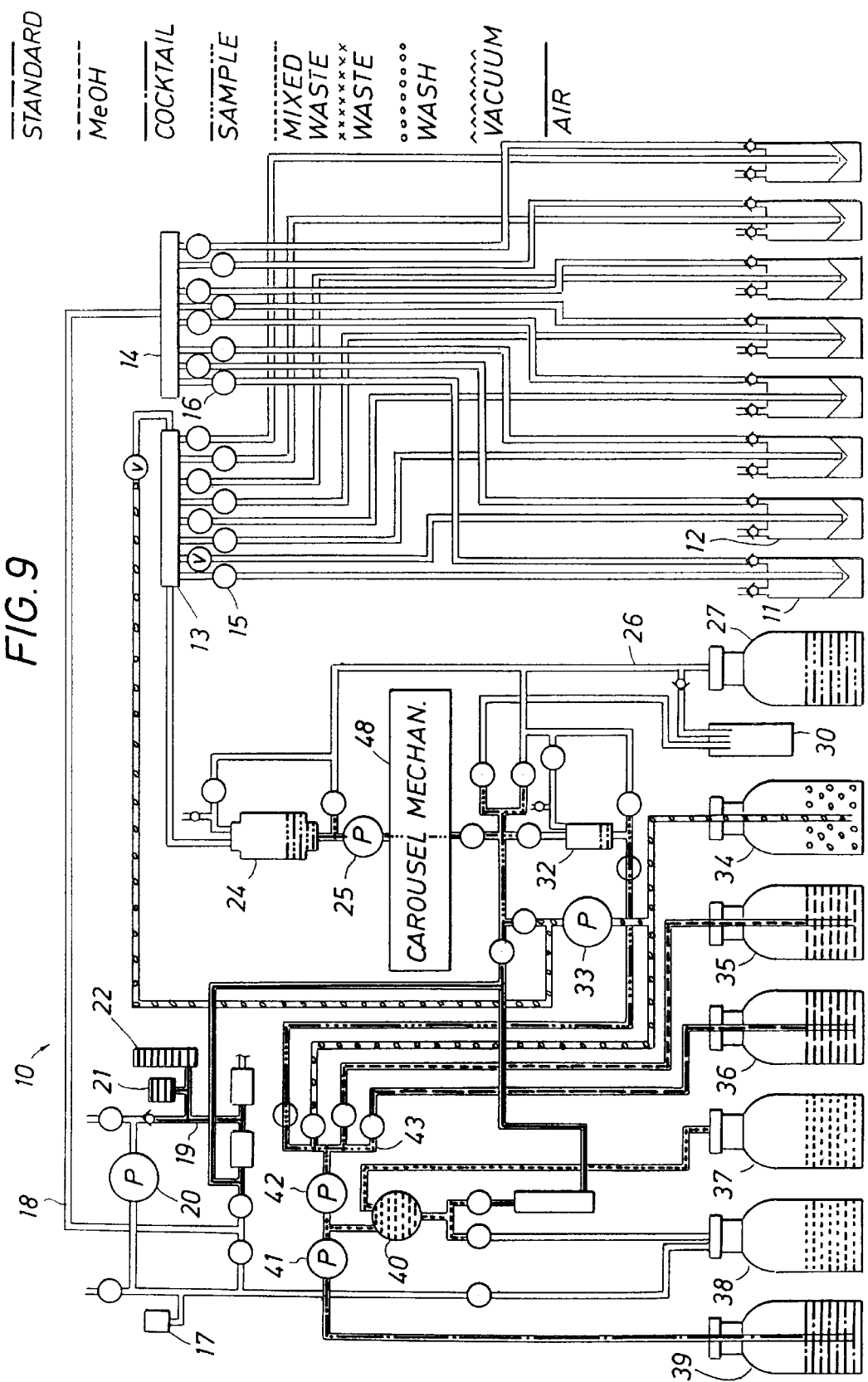
Figure 10:
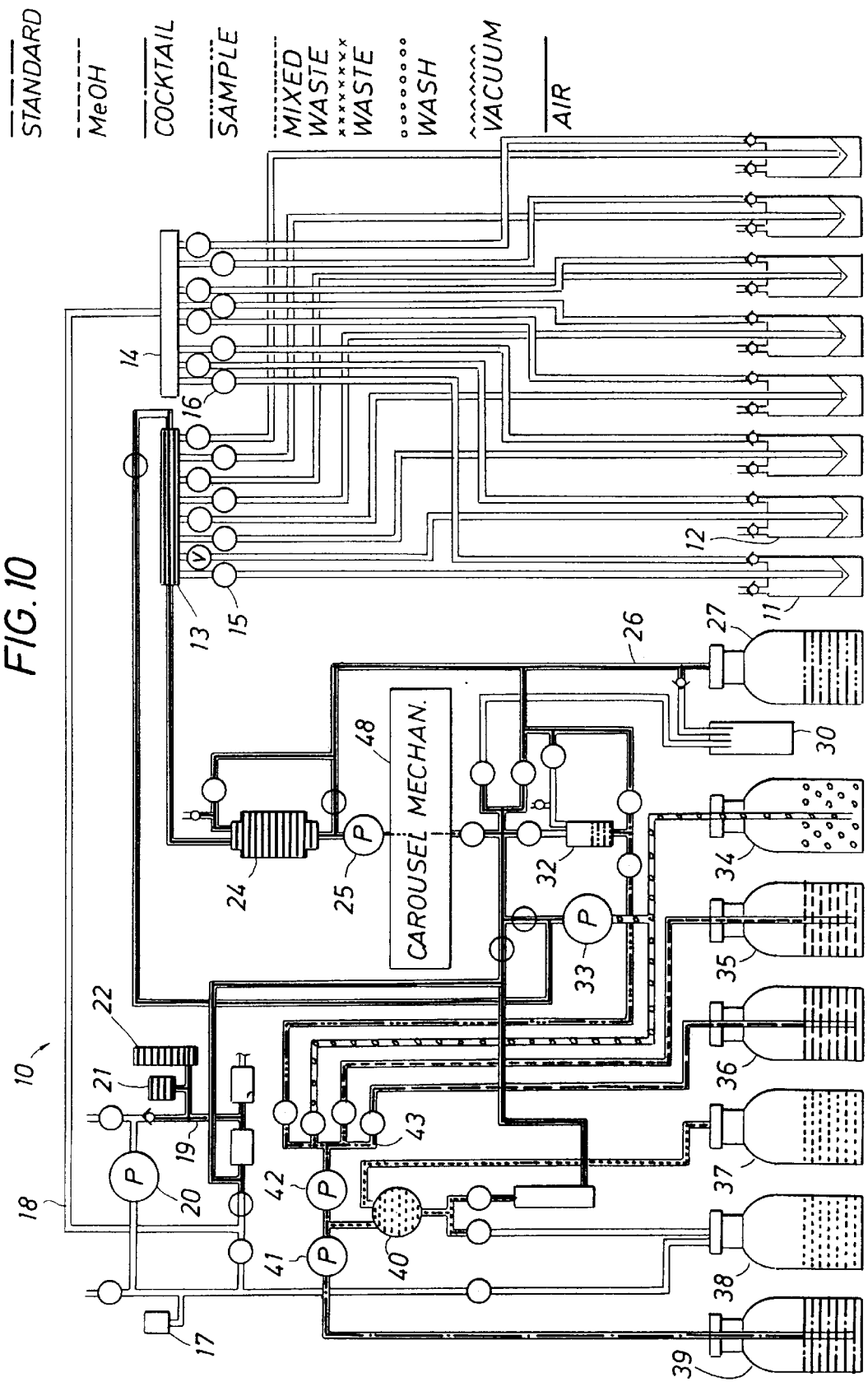

FIG. 3 shows the delivery of air through the line 18. This air, under pressure, forces the sample out of the pump 11, through the manifold 13 and into the container 24. As stated before, this container holds the sample and preferably captures a measured amount, i.e., 50 cc in this embodiment. FIG. 4 shows surplus sample is delivered to the waste container 27. FIG. 5 then shows how the sample is directed from the sample container 24 into the container 32 through the carousel 48 for any requisite pretreatment. The progression from FIG. 5 to FIG. 6 then leads to the step shown in FIG. 7 which is pumping a specified sample such as 10 ml into the sample container 30. FIG. 8 is similar to FIG. 7 and shows preparation for cleaning the sample line 13. Continuing in FIG. 9, the pump 42 is operated to fill the counting chamber 40 from the container 32. Surplus is dumped in the container 37. Ideally, there should be no surplus because the container 32 holds a measured quantity. FIG. 10 shows the counting chamber 40 with the sample in it so that radiation counts are totaled and stored for a fixed interval. In another portion of the system 10, air from the pump 20 is delivered through the manifold 13 and elsewhere to blow out the lines and clear the chambers. This helps purge any remnant materials. The purge is further assisted by delivery of a wash liquid from the wash source 34 which is delivered from it through the pump 33 and ultimately through the manifold 13, the chamber 24 and into the waste container 34. In other words, washing of these lines occurs while counting is going on at the counting cell 40.

Figure 11:
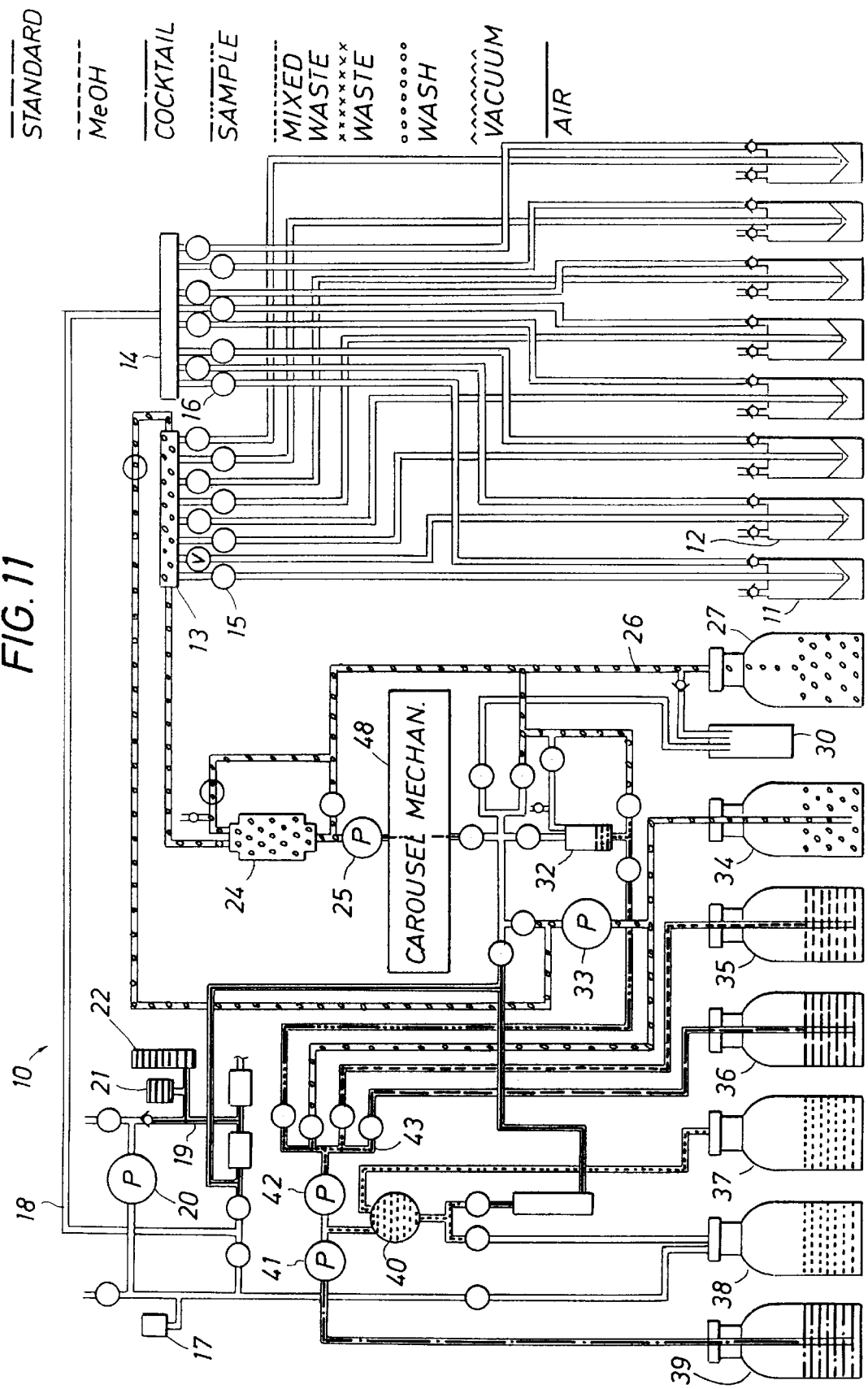
Figure 12:
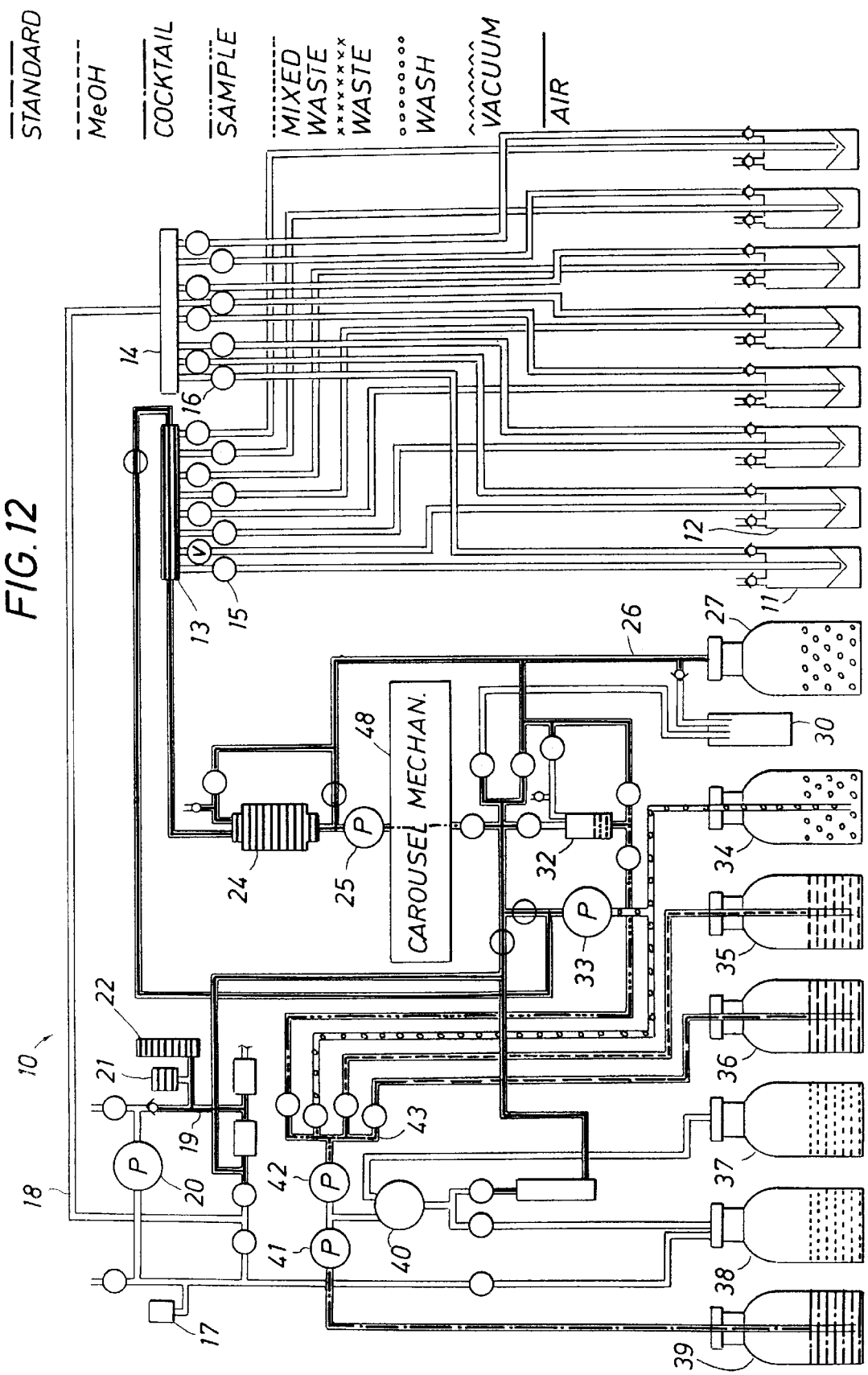
Figure 13:
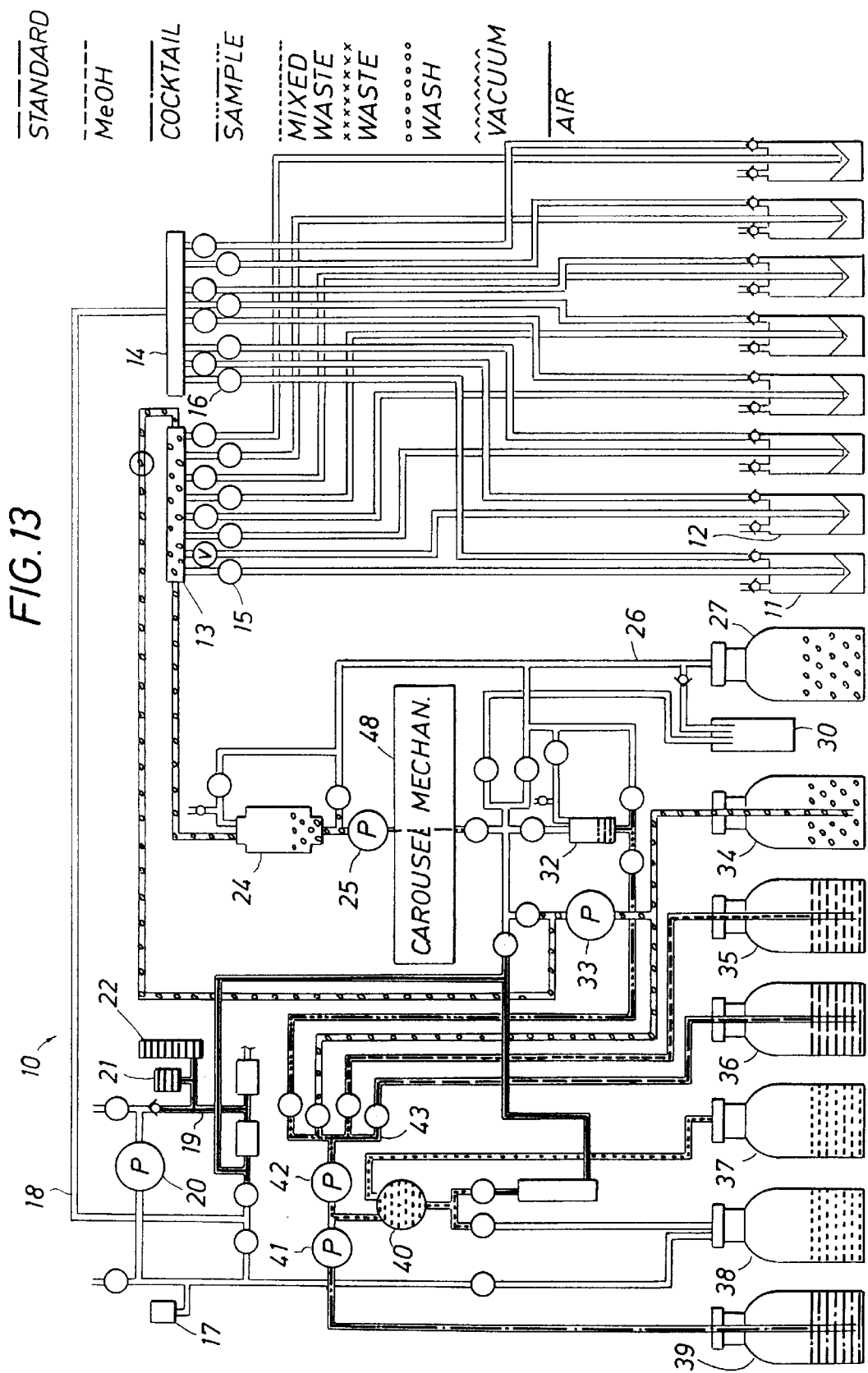
Figure 14:
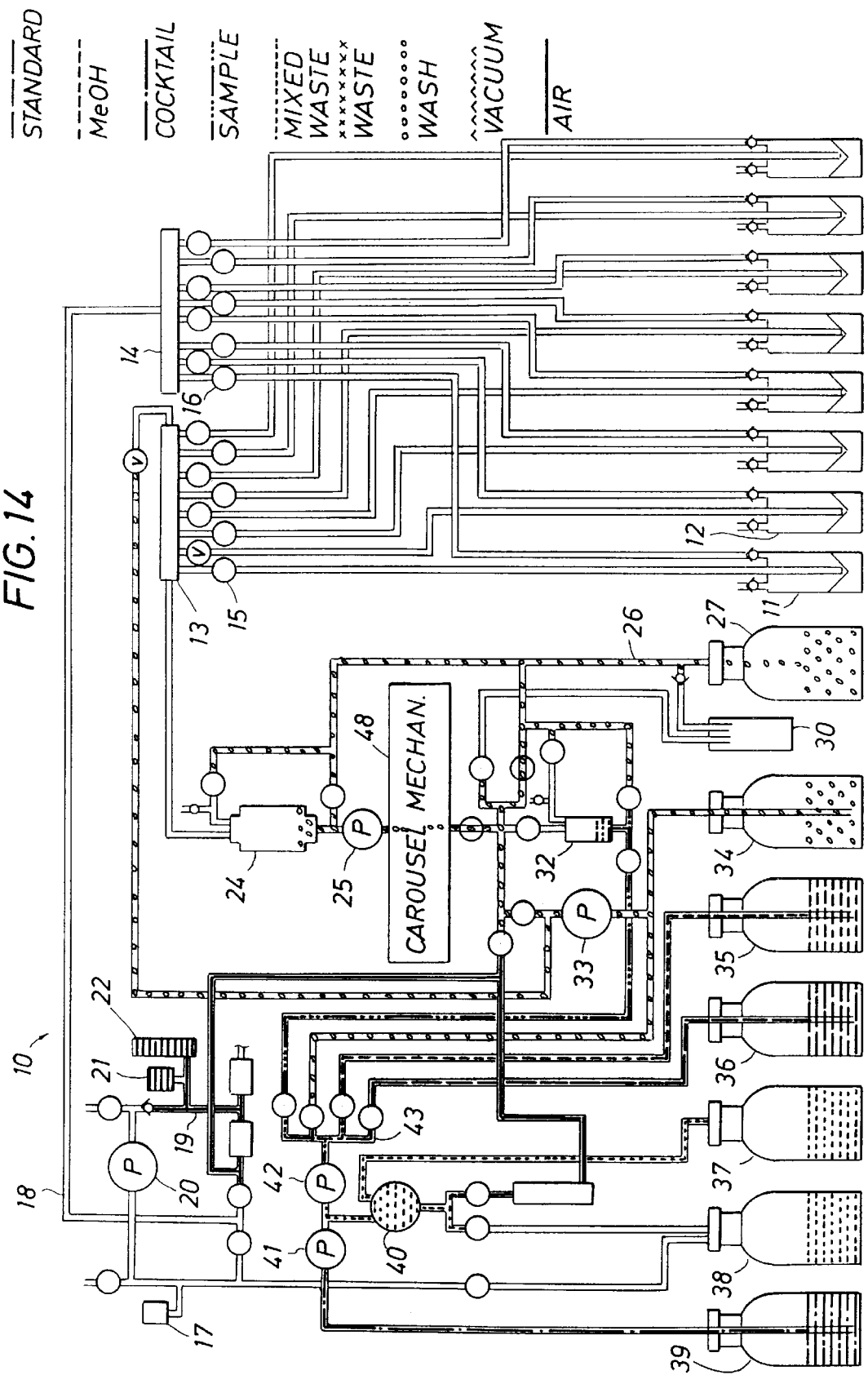
Figure 15:
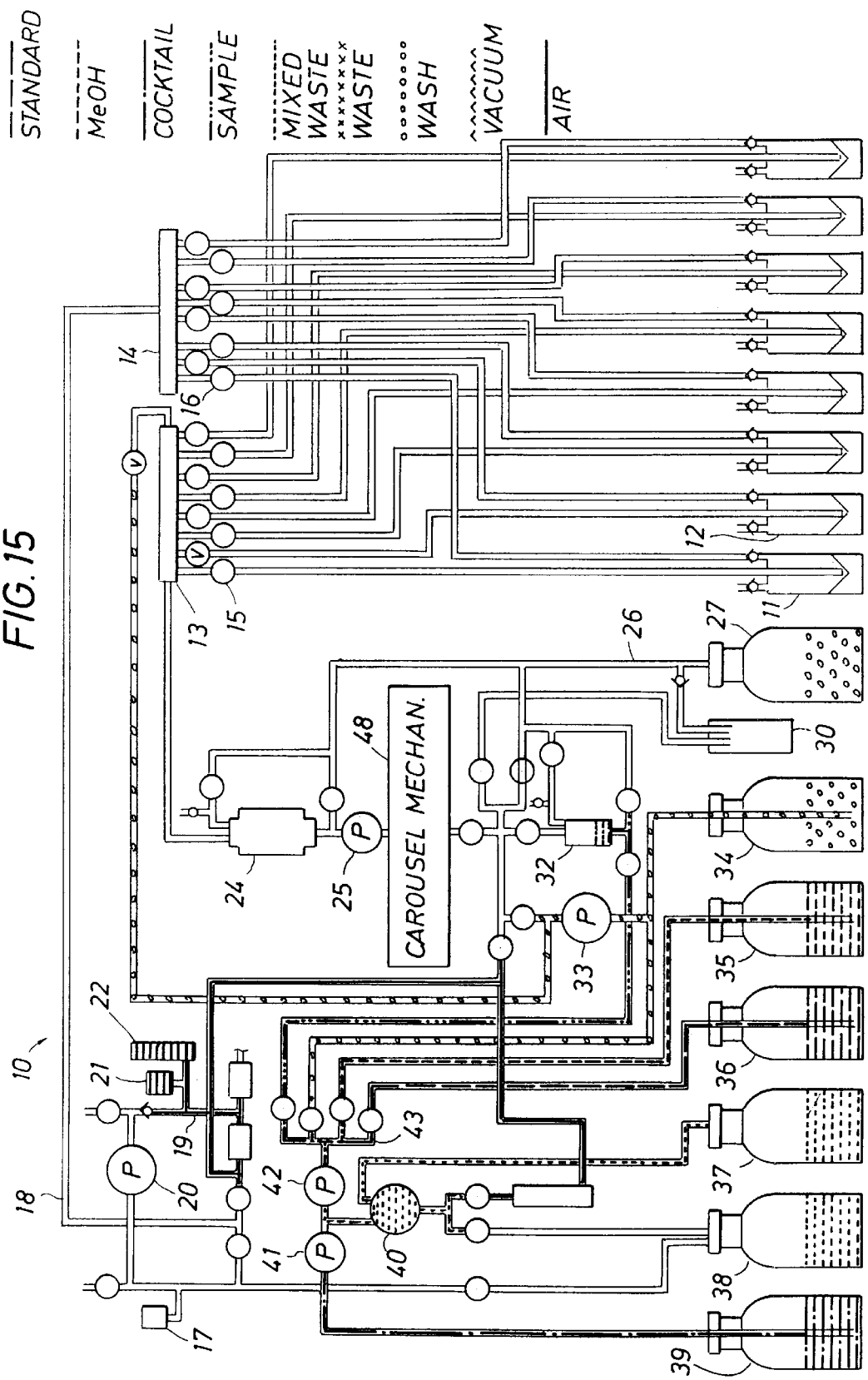
Figure 16:
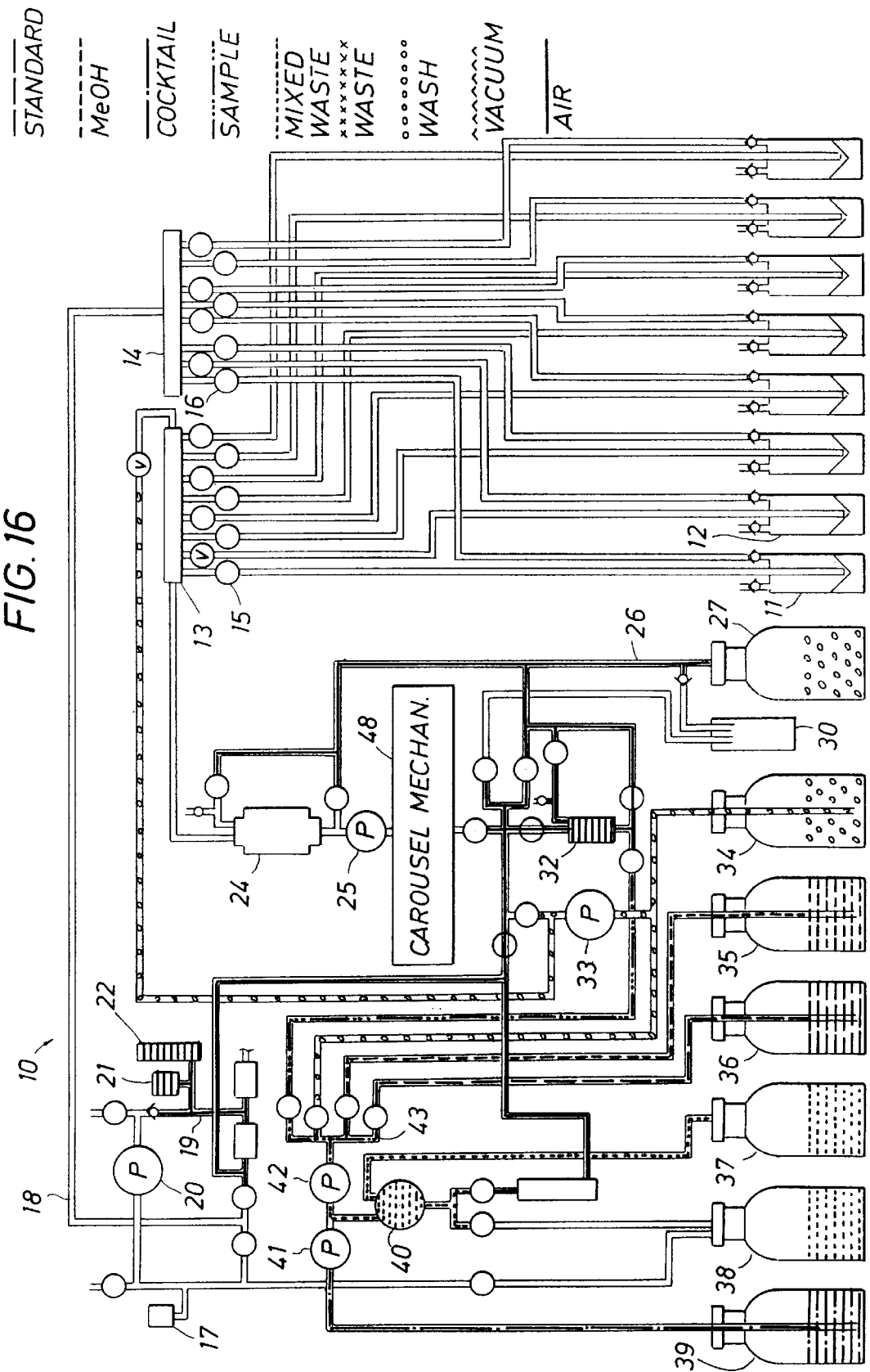

After that wash cycle in those specified lines shown in FIG. 11, another air dry sequence occurs as illustrated in FIG. 12. Again, this can be conducted while the cell 40 holds the sample and counting continues. As will be understood, counting cannot be rushed; it requires a finite interval to measure a statistically meaningful number of counts in the chance that the water sample in the chamber 40 includes tritium. Accordingly, an air dry sequence occurs in FIG. 12 and another wash sequence is then initiated thereafter as illustrated in FIG. 13. FIG. 14 shows that the wash water is delivered to the waste container 34 after the sequence shown in FIG. 13. FIG. 14 shows the continuation of this and the next step which is permitting an interval of time so that the container 24 has time to dry. FIG. 16 shows the start of this drying sequence in which air is delivered through selected lines for air drying.

Figure 17:
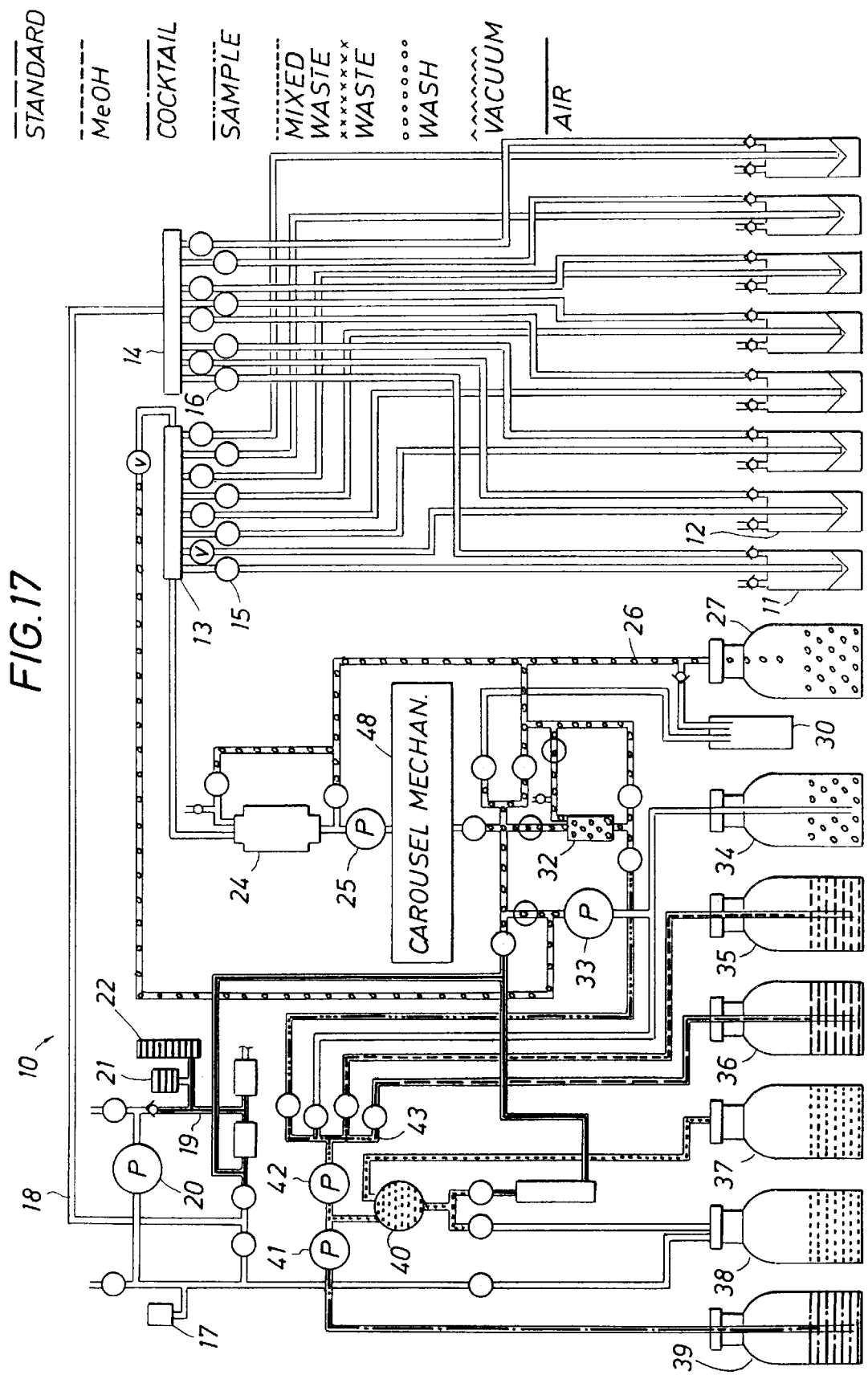
Figure 18:
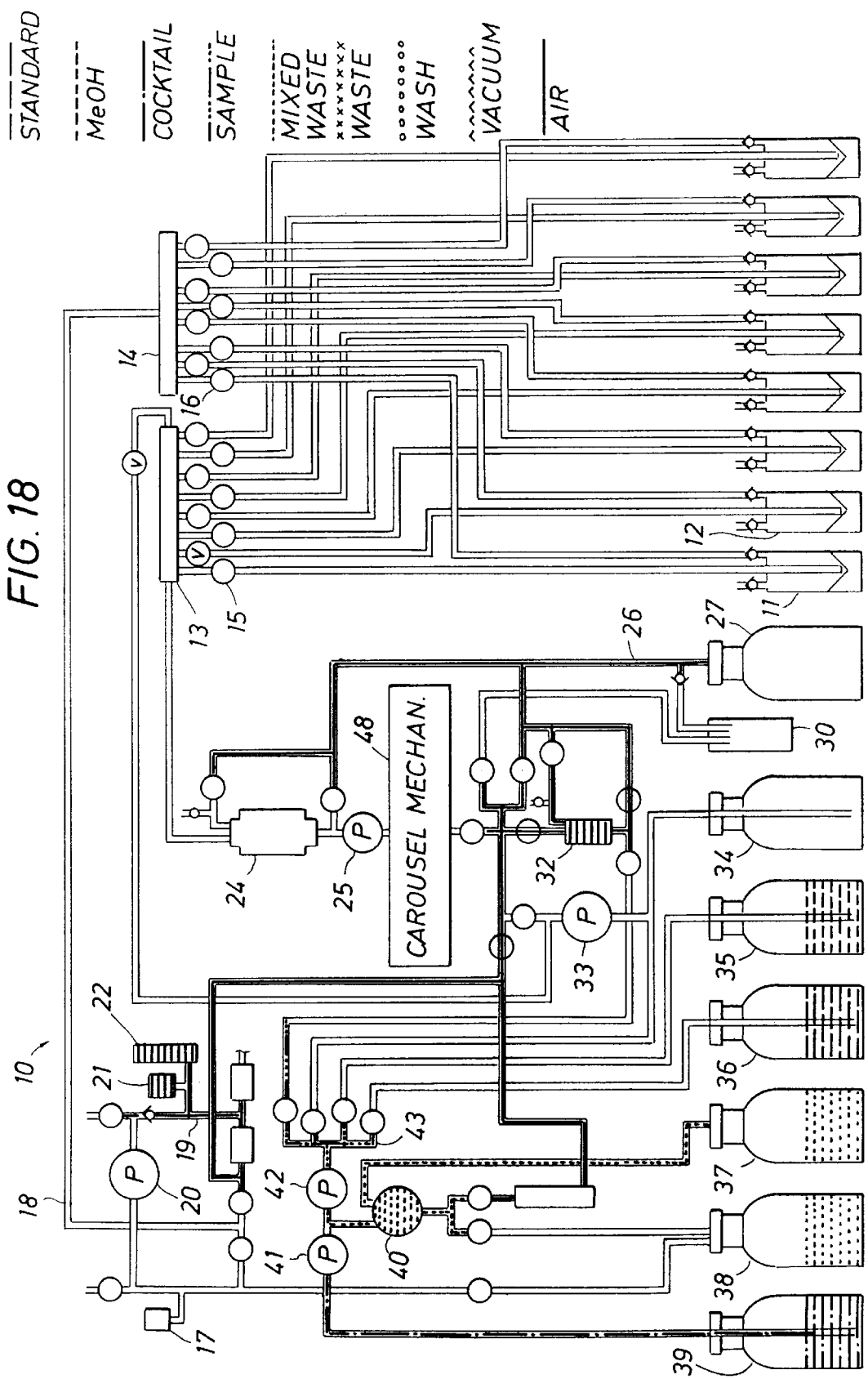
Figure 19:
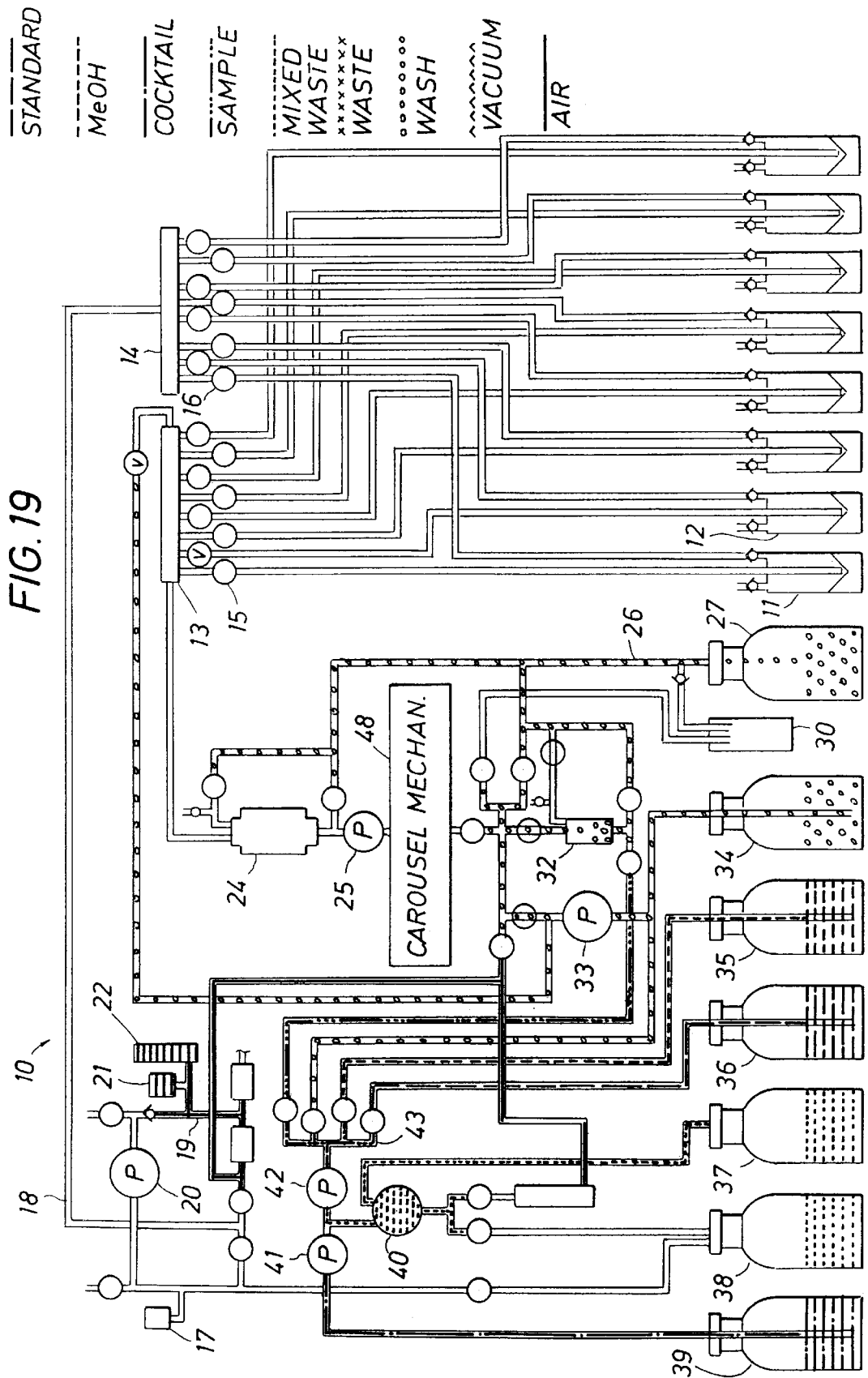
Figure 20:
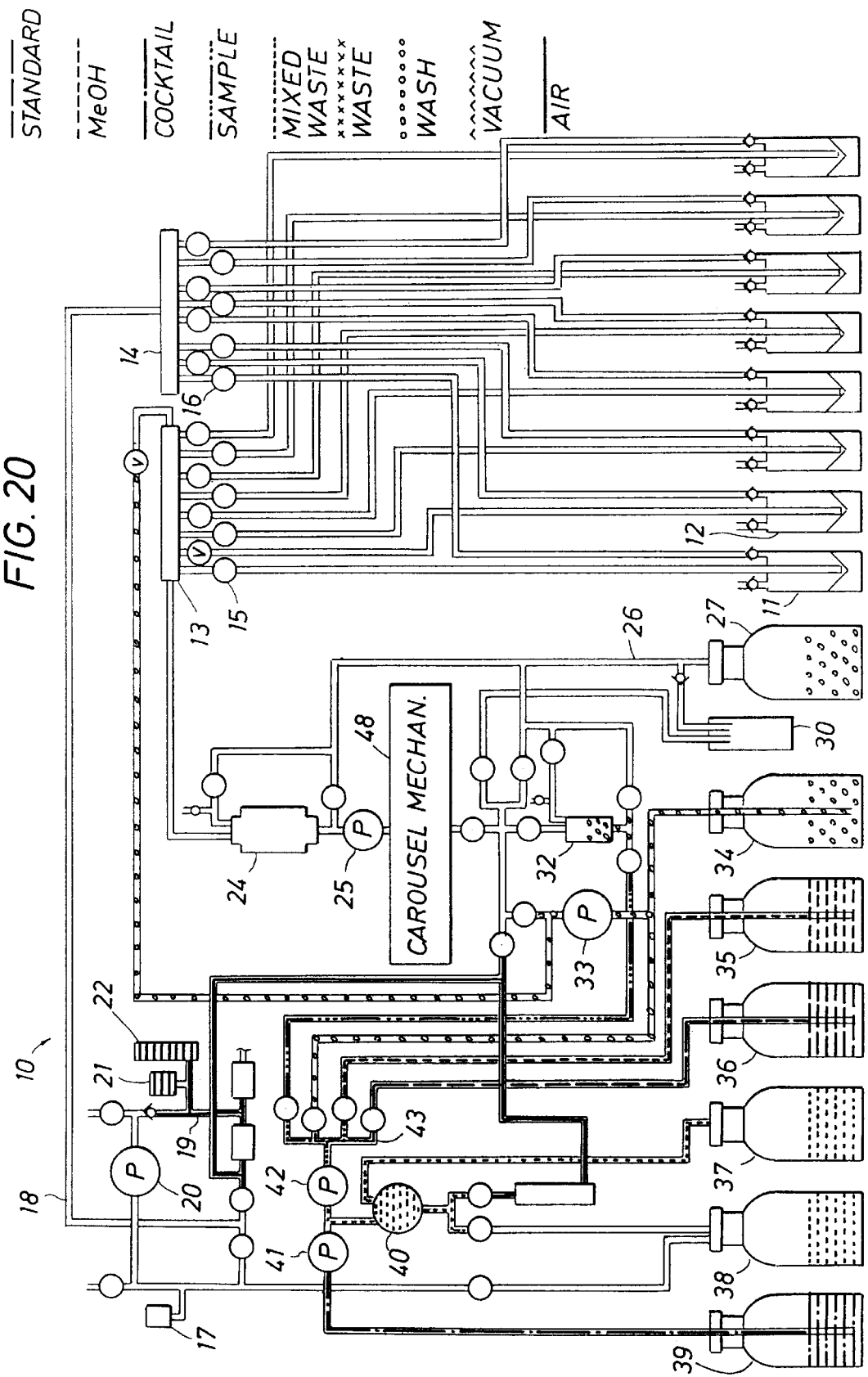
Figure 21:
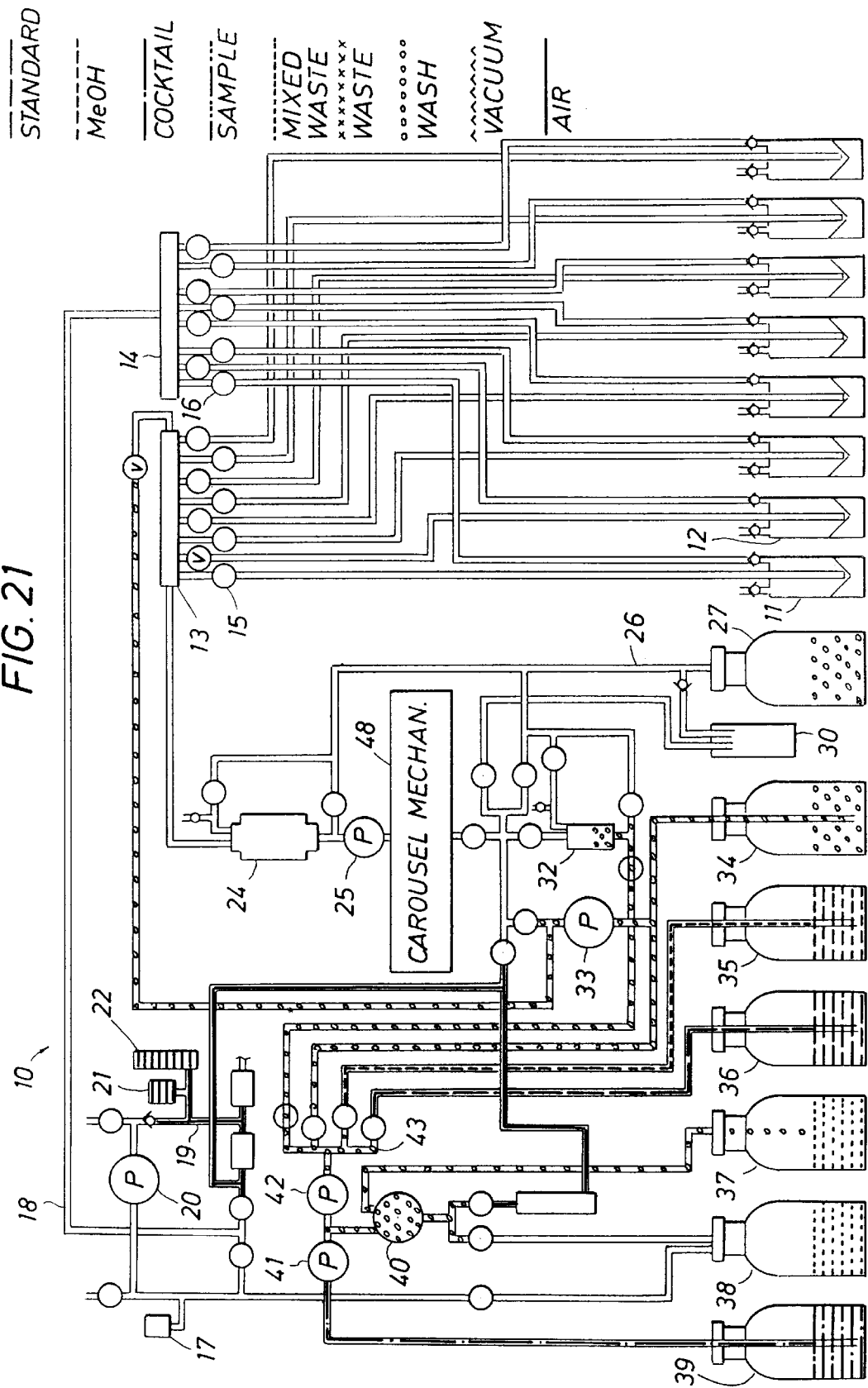

FIG. 17 shows another wash step. In this particular instance, the measured sample container 32 is washed. Previously, the container 24 had been washed. Therefore, the washing sequence illustrated in FIG. 17 is then terminated and an air drying sequence is initiated as shown in FIG. 18. All the while, counting continues of any radioactivity from the sample in the cell 40. FIG. 19 is contrasted with FIG. 18 which shows air drying; FIG. 19 shows a second wash cycle. This leads then to the operative status shown in FIG. 20 from FIG. 19. This repairs the system so that wash water is then directed through the counting cell 40 to flush out the prior sample. This occurs at the end of the counting sequence. If, for instance, five or ten minutes are required for counting, the sample is left in the cell 40 for that interval. The interval is one scale factor as are the size of the sample, the sensitivity of the test instrument and the like. When finished, the sample is washed out so that the wash water from the source 34 is delivered, under pressure, through the cell 40. FIG. 21 shows that the cell 40 has been provided with the wash water and it is then vented from that cell into the waste container 37.

Figure 22:
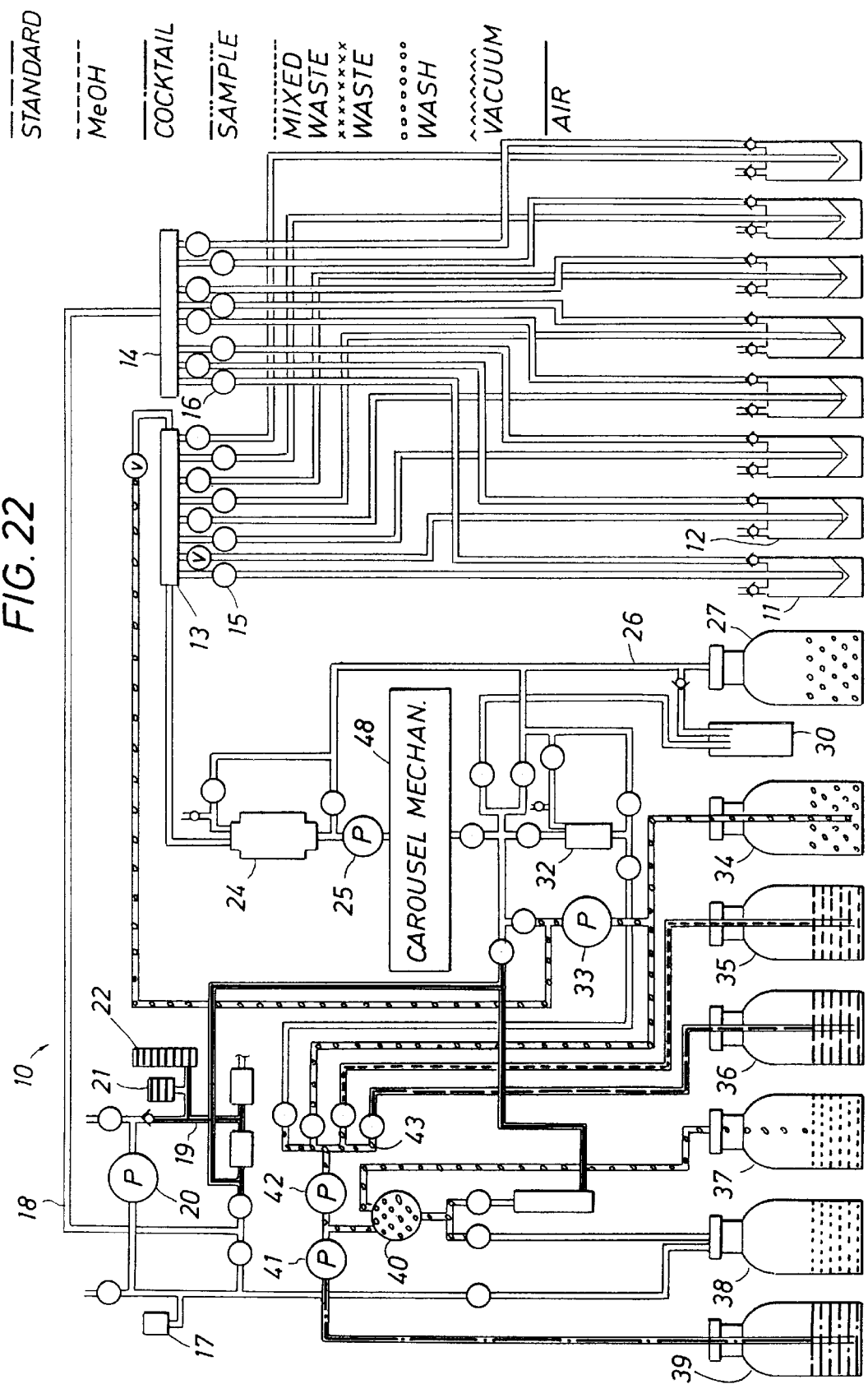
Figure 23:
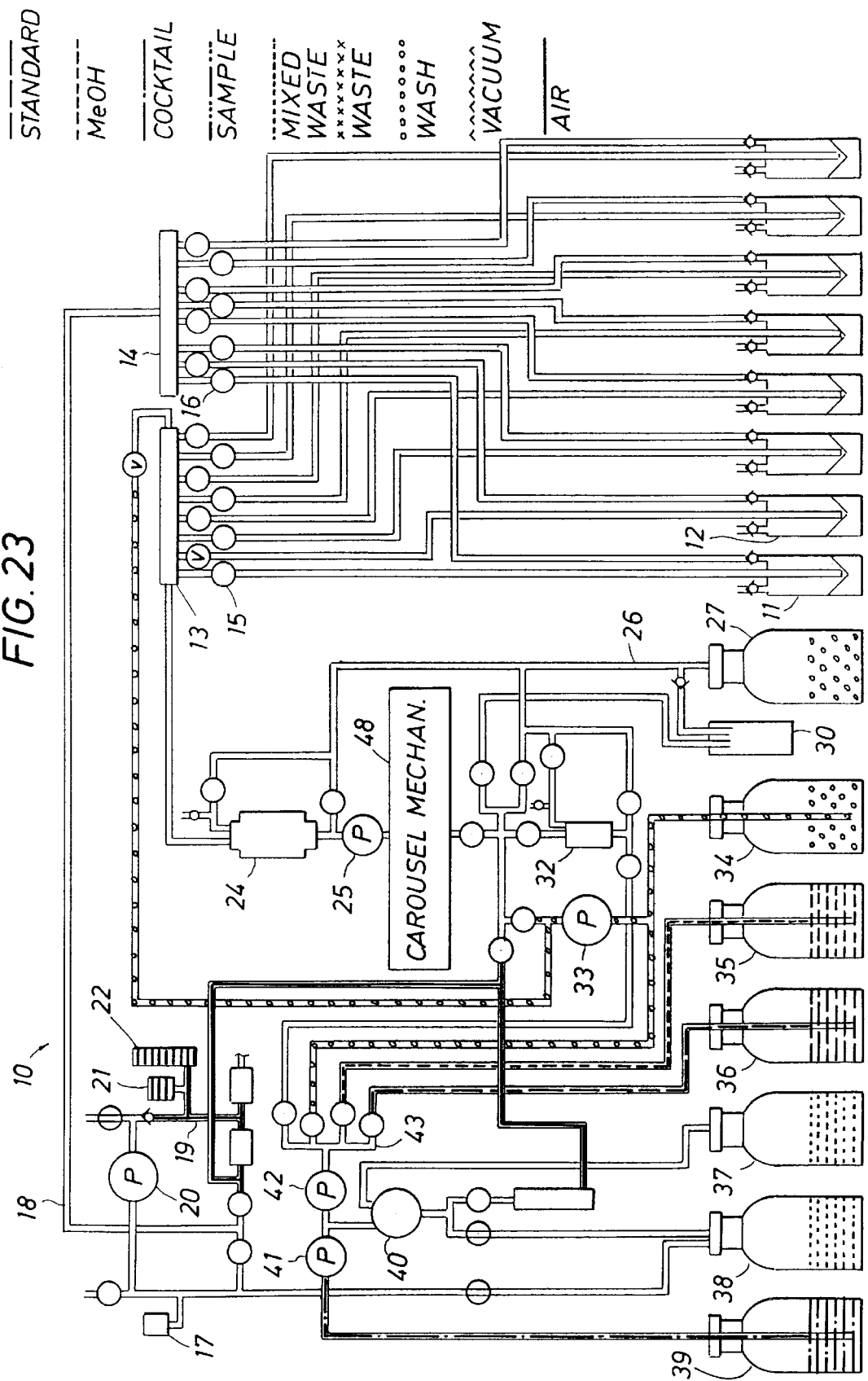
Figure 24:
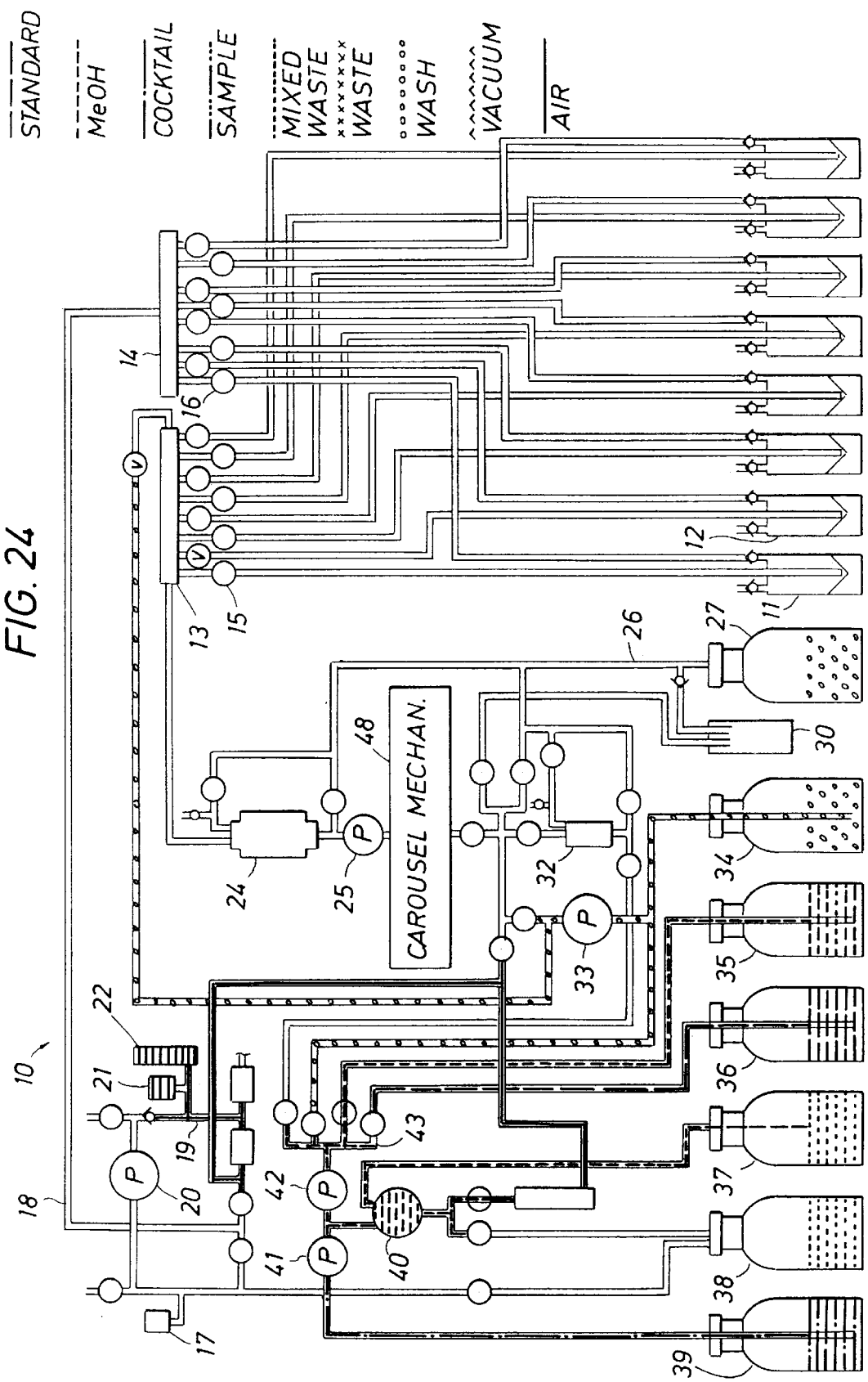
Figure 25:
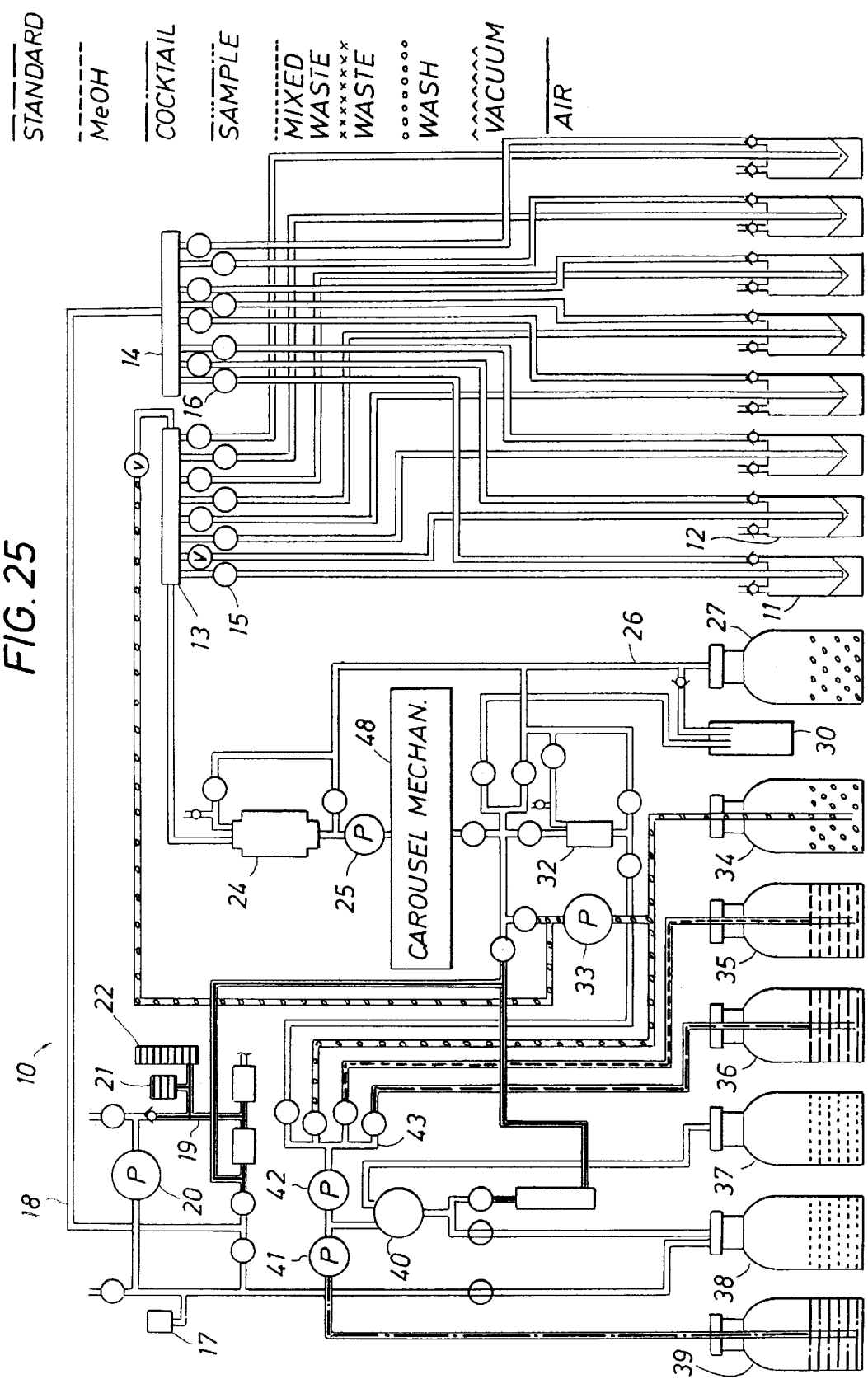

After the wash water is put into the cell 40, it is then forced out as shown in FIG. 22. It is empty as illustrated in FIG. 23. This sequence is repeated with a second or alternate wash from the source 35 delivered through the cell 40. When this step of FIG. 25 is completed, the chamber 40 is then empty. When the condition of FIG. 25 is achieved, the equipment has operated one full cycle and is then returned to the state of affairs shown in FIG. 1. Then, this or some other sequence can be executed again.

Speaking in summary terms, it will be observed that two wash cycles are applied in most critical areas. Dry cycles are intermeshed between wash cycles. This provides a high level of cleanliness. This prevents a first sample from cross-contaminating second and third samples. This assures that the data from a first sample will not blur into the data for a second and following samples. This also operates to provide data for each of the samples as well as a demounted sample in the container 30 if so desired. The sample container 30 can be filled from time to time and moved to another location.

The system 10 is more readily built, maintained, operated and repaired. It includes less costly valves. Moreoveri it is constructed with the manifolds 13 and 14 which can be replicated where N is increased to a different number. Finally, the system 10 enables ready recovery of the samples with testing occurring as rapidly as possible depending on the nature and duration required for the particular test.

While the foregoing disclosure is directed toward preferred embodiments, the scope of the invention is set forth by the claims which follow.

I claim:

1. A method for repetitively testing a liquid sample from at least two sample sources comprising the steps of:
    (a) pneumatically charging a first sample gathering mechanism installed to collect ground water wherein a liquid sample is collected therein from a first liquid sample source;
    (b) transferring the first liquid sample along a liquid sample transfer line so that said first liquid sample is delivered through a sample input manifold for a liquid chamber;
    (c) measuring a controlled quantity of the first liquid sample input to said liquid chamber;
    (d) adding a measured quantity of reagent to the measured quantity of the first liquid sample;
    (e) directing the sample from the liquid chamber to a test instrument to measure an aspect of the first liquid sample;
    (f) purging the first liquid sample with a fluid flow to clear said transfer line, said sample input manifold, said chamber and said test instrument of any residue from the first liquid sample;

(g) pneumatically charging a second sample gathering mechanism to collect a liquid sample from a second liquid sample source; and (h) repeating steps (b), (c), (d), (e), and (f) for the second liquid sample.

2. The method of claim 1 wherein the step of charging at least two sample gathering mechanisms with pressure to initiate sample flow wherein each of said sample gathering mechanisms delivers liquid sample through assigned sample delivery lines connected to said sample input manifold, and the sample input manifold operatively and sequentially delivers without mixing the first and then second liquid samples.

3. The method of claim 2 including the step of connecting N sample line input valves to N sample input lines and said manifold so that only one liquid sample is received at a time, and including the step of serially transferring liquid samples from said manifold so that only serial measurements occurs at said test instrument.

4. The method of claim 1 including the step of measuring by obtaining a liquid sample greater in size than a specified sample size, placing the liquid sample in said chamber, and then removing only the specified size sample therefrom, and thereafter mixing with said measured quantity of reagent, and then operating the sample test instrument sufficiently long to make the measurement after receiving the sample.

5. The method of claim 4 wherein said sample receiving chamber connects to a sample liquid flow line to deliver consecutive samples into a sized chamber.

6. The method of claim 1 wherein each of said sample gathering mechanisms is connected to two lines wherein:

(i) the first line is pneumatically operates said mechanism;

(j) the second line delivers the sample therefrom; and including the sequential steps of:

(k) transferring pneumatic charge through the first line;

(l) forcing the liquid sample from said mechanism with the pneumatic charge;

(m) timing opening of a first line valve and a second line valve so that the liquid sample is input to and through the sample input manifold; and (n) after liquid sample is transferred from said sample gathering mechanism, isolating said mechanism by closing said first and second line valves.

7. The method of claim 1 including the step of placing the reagent in a container and flowing the sample through the container serially into a container of limited capacity, and also providing a new reagent and reagent container for each sample.

8. The method of claim 7 including the step of positioning multiple reagent containers on a rotatable carousel to thereby position reagent containers for sample reagent treatment.

9. The method of claim 1 including the steps of serially processing multiple liquid samples in said test instrument and including the step of liquid and air purging of said test instrument prior to sample processing.

10. The method of claim 1 wherein said step of placing a sample in the test instrument for a specified time interval to enable emitted radiation to be summed over time, and wherein said test instrument includes a radiation measurement device.

11. The method of claim 1 including the steps of serially and in sequence;

(i) transferring the liquid sample;

(j) storing the sample in the chamber;

(k) mixing the sample with the reagent;

(l) placing sample in a sized container;

(m) pumping the sample to the test instrument;

(n) holding the sample in the test instrument for testing; and (o) dumping the sample after testing.

12. The method of claim 11 wherein the sample flows along a liquid feed line for each of steps (i) to (m).

13. The method of claim 12 wherein each of the liquid feed lines involved in steps (j) to (m) is purged with a wash liquid and then is dried with gas flow prior to testing a second liquid sample through by repeating steps (i) to (o) of claim 11.

14. The method of claim 13 including the step of controlling purging of the feed lines so that wash liquid is followed with air flow for drying.

15. The method of claim 1 wherein the liquid samples are obtained from N sample gathering mechanisms, and delivered in a selected sequence to the test instrument to test for decay of radioactive hydrogen measured by summing over time hydrogen originated decay events; and indicating for the liquid samples the measured radioactivity.

16. The method of claim 15 wherein each of said N sample gathering mechanisms is placed at locations around a nuclear facility to detect radioactive ground or waste water.

17. The method of claim 16 wherein some of the mechanisms are placed in wells to sample ground water.

18. The method of claim 17 wherein some of the ground water mechanisms are underground, and positive air pressure operates them to lift ground water to the surface.

19. The method of claim 15 including the step of repetitively over time obtaining repeated samples from said N mechanisms.

* * * * *